(12) United States Patent
Weese-Mayer et al.

(10) Patent No.: US 7,393,642 B2
(45) Date of Patent: Jul. 1, 2008

(54) METHODS AND PRIMERS FOR DIAGNOSING IDIOPATHIC CONGENITAL CENTRAL HYPOVENTILATION SYNDROME

(75) Inventors: Debra E. Weese-Mayer, Chicago, IL (US); Elizabeth M. Berry-Kravis, Des Plaines, IL (US); Lili Zhou, Darien, IL (US)

(73) Assignee: Chicago Community Foundation, Chicago, IL (US)

( * ) Notice: Subject to any disclaimer, the term of this patent is extended or adjusted under 35 U.S.C. 154(b) by 204 days.

(21) Appl. No.: 10/891,585

(22) Filed: Jul. 15, 2004

(65) Prior Publication Data

US 2005/0042657 A1 Feb. 24, 2005

Related U.S. Application Data

(60) Provisional application No. 60/488,105, filed on Jul. 17, 2003.

(51) Int. Cl.
C07H 21/04 (2006.01)
C12Q 1/68 (2006.01)
(52) U.S. Cl. .................. 435/6; 435/91.1; 435/91.2
(58) Field of Classification Search .................. None
See application file for complete search history.

(56) References Cited

U.S. PATENT DOCUMENTS 6,251,589 B1 * 6/2001 Tsuji et al. ............... 435/6
2003/0092019 A1 * 5/2003 Meyer et al. .............. 435/6

OTHER PUBLICATIONS

Ioannidis (Nature Genetics, vol. 29, pp. 306-309, Nov. 2001).*
Hirschhorn et al. (Genetics in Medicine. vol. 4, No. 2, pp. 45-61, Mar. 2002).*
Amiel et al. (Nature Genetics, vol. 33, pp. 1-3, Mar. 17, 2003).*
Genbank Accession No. BAA82670, Aug. 1999.*
Adachi et al., "Paired-like homeodomain proteins Phox2a/Arix and Phox2b/NBPhox have similar genetic organization and independently regulate dopamine beta-hydroxylase gene transcription," *DNA Cell Biol.*, 19(9):539-554 (2000).
Amiel et al., "Polyalanine expansion and frameshift mutations of the paired-like homeobox gene PHOX2B in cogenital central hypoventilation syndrome," *Nature*, 33: 1-3 (2003).
Garcia-Barceló et al., "Association study of PHOX2B as a candidate gene for Hirschsprung's disease," *Gut*, 52: 563-567 (2003).
Gaultier et al., "Genetics and respiratory control: Studies in normal humans and genetically modified animals," *Rev Mal Respir*, 20: 77-94 (2003).
Goodman et al., "Human HOX gene mutations," *Clinical Genetics*, 59: 1-11 (2001).
Guillemot et al., "Dynamic expression of the murine Achaete-Scute homologue Mash-1 in the developing nervous system," *Mechanisms of Development*, 42: 171-185 (1993).

Guillemot et al., "Mammalian achaete-scute Homolog 1 is required for the early development of olfactory and autonomic neurons," *Cell*, 75: 463-478 (1993).
Haddad et al., "Congenital failure of automatic control of ventilation, gastrointestinal motility and heart rate," *Medicine*, 57(6): 517-26 (1973).
Huber et al., "Generation of neuroendocrine chromaffin cells from sympathoadrenal progenitors," *Ann NY Acad Sci*, 971: 554-559 (2002).
Johnson et al., "Two rat homologues of Drosophila achaete-scute specifcally expressed in neuronal precursors," *Nature*, 345: 358-361 (1990).
Kanai et al., "Congenital central hypoventilation syndrome: a novel mutation of the RET gene in an isolated case," *Tohoku J Exp Med*, 196: 241-246 (2002).
Kitamura et al., "Mutation of ARX causes abnormal development of forebrain and testes in mice and X-linked lissencephaly with abnormal genitalia in humans" *Nat Genet*, 32: 359-69 (2002).
Lo et al., "Specification of neurotransmitter identity by Phox2 proteins in neural crest stem cells," *Neuron*, 22: 693-705 (1999).
Lo et al., "Mash1 maintains competence for BPM2-induced neuronal differentiation in post-migratory neural crest cells," *Current Biol*, 7: 440-450 (1997).
Pattyn et al., "The homeobox gene Phox2b is essential for the development of autonomic neural crest derivatives," *Nature*, 399: 366-370 (1999).
Stromme et al., "Mutations in the human ortholog of Aristaless cause X-linked mental retardation and epilepsy," Nat Genet, 30: 441-445 (2002).
Weese-Mayer et al., "Idiopathic cogenital central hypoventilation syndrome: Analysis of genes pertinent to early automatic nervous system embryologic development and identification of mutations in PHOX2b," *Am J Med Gen*, 123A: 267-278 (2003).
Weese-Mayer et al., "Genetics of cogenital central hypoventilation syndrome: Lessons from a seemingly orphan disease," *Am J Respir Crit Care Med*, 170: 16-21 (2004).
Yokoyama et al., "Genomic structure and functional characterization of NBPhox (PMX2B), a homeodomain protein specific to catecholaminergic cells that is involved in second messenger-mediate transcriptional activation," *Genomics*, 59 (1), 40-50 (1999).
Young et al., "Expression of Ret-p75NTR, Phox2a-, Phox2b-, and tyrosine hydroxylase-immunoreactivity by undifferentiated neural crest-derived cells and different classes of enteric neurons in the embryonic mouse gut," *Developmental Dynamics*, 216: 137-152 (1999).

(Continued)

*Primary Examiner*—Jeanine A Goldberg
(74) *Attorney, Agent, or Firm*—Barnes & Thornburg LLP; Alice O. Martin

(57) ABSTRACT

The present invention provides assays and kits for diagnosing idiopathic congenital central hypoventilation syndrome. The present assays and kits focus on the second polyalanine repeat of the PHOX2b gene or gene product, which is normally 20 residues in length. A polyalanine repeat 25 to 33 residues in length is strongly correlated with idiopathic congenital central hypoventilation syndrome.

11 Claims, 4 Drawing Sheets

OTHER PUBLICATIONS

Zec et al., "Expression of the homeobox-containing genes EN1 and EN2 in human fetal midgestational medulla and cerebellum," *J Neuropathol and Exper Neurol*, 56: 236-242 (1997).

Amiel et al., 1998. Mutations of the RET-GDNF signaling pathway in Ondine's curse. Am J Hum Genet 62:715-717.

Bienvenu et al., 2002. ARX, a novel Prd-class-homeobox gene highly expressed in the telencephalon, is mutated in X-linked mental retardation. Hum Mol Genet 11:981-91.

Dubreuil et al., 2002. The role of Phox2b in synchronizing panneuronal and type-specific aspects of neurogenesis. Development 129:5241-5253.

Faure et al., 2002. Abnormal esophageal motility in children with congenital central hypoventilation syndrome. Gastroenterology 122:1258-1263.

Fitze et al., 2003. Association of germline mutations and polymorphisms of the RET proto-oncogene with idiopathic congenital central hypoventilation syndrome in 33 patients. J Med Genet 40:E10.

Hirsch et al., 1998. Control of noradrenergic differentiation and Phox2a expression by MASH1 in the central and peripheral nervous system. Development 125:599-608.

Lo et al., 2002. Comparison of the generic neuronal differentiation and neuron subtype specification functions of mammalian achaetescute and atonal homologs in cultured neural progenitor cells. Development 129:1553-1567.

Lo et al., 1998. MASH1 activates expression of the paired homeodomain transcription factor Phox2a, and couples panneuronal and subtype-specific components of autonomic neuronal identity. Development 125:609-620.

Nickerson et al., 1997. PolyPhred: automating the detection and genotyping of single nucleotide substitutions using fluorescence-based resequencing. Nucleic Acids Res 25:2745-2751.

Pattyn et al., 1997. Expression and interactions of the closely related homeobox genes Phox2a and Phox2b during neurogenesis. Development 124:4065-4075.

Renolleau et al., 2001. Impaired ventilatory responses to hypoxia in mice deficient in endothelin-converting-enzyme-1. Pediatr Res 49:705-712.

Sakai et al., 1998. Point mutation in exon 12 of the receptor tyrosine kinase proto-oncogene RET in Ondine-Hirschsprung syndrome. Pediatrics. 101:924-926.

Simon et al., 2001. Fate of midbrain dopaminergic neurons controlled by the engrailed genes. J of Neurosci 21:3126-3134.

Sritippayawan et al., 2002. Mother-daughter transmission of congenital central hypoventilation syndrome. Am J Respir Crit Care Med. 166: 367-369.

Stanke et al., 1999. The Phox2 homeodomain proteins are sufficient to promote the development of sympathetic neurons. Development 126:4087-4094.

* cited by examiner

METHODS AND PRIMERS FOR DIAGNOSING IDIOPATHIC CONGENITAL CENTRAL HYPOVENTILATION SYNDROME

CLAIM OF PRIORITY

This application claims priority from U.S. Provisional Patent Application No. 60/488,105, filed Jul. 17, 2003, the entire teachings of which are incorporated by reference.

FIELD OF THE INVENTION

The present invention relates to assays and methods for diagnosing and confirming the diagnosis of idiopathic congenital central hypoventilation syndrome.

BACKGROUND OF THE INVENTION

Idiopathic congenital central hypoventilation syndrome (CCHS, also known as central hypoventilation syndrome, Haddad syndrome and the literary misnomer "Ondine's curse"; MIM number: 209880, date last edited Jun. 14, 2004) is an unique disorder of respiratory control [Guilleminault et al., 1982; Haddad et al., 1978; Mellins et al., 1970; Paton et al., 1989; Shannon et al., 1976; Weese-Mayer et al., 1992; Weese-Mayer et al., 1999], occurring in association with Hirschsprung disease (HSCR) [Bower et al., 1980; Commare et al., 1993; Haddad et al., 1978; Hamilton et al., 1989; Guilleminault et al., 1982; Minutillo et al., 1989; O'Dell et al., 1987; Stern et al., 1980; Verloes et al., 1993; Weese-Mayer et al., 1992], tumors of neural crest origin [Bower et al., 1980; Commare et al., 1993; Haddad et al., 1978; Swaminathan et al., 1989; Weese-Mayer et al., 1992] (neuroblastoma, ganglioneuroblastoma, ganglioneuroma), and symptoms of diffuse autonomic nervous system dysfunction (ANSD) [Weese-Mayer et al., 2001] including decreased heart rate variability [Ogawa et al., 1993; Silvestri et al., 2000; Woo et al., 1992], an attenuated heart rate response to exercise [Silvestri et al., 1995], severe constipation [Weese-Mayer et al., 1992], esophageal dysmotility/dysphagia [Faure et al., 2002], decreased perception of discomfort, pupillary abnormalities [Goldberg et al., 1996; Weese-Mayer et al., 1992], decreased perception of anxiety [Pine et al., 1994], sporadic profuse sweating, and decreased basal body temperature among others. Subsequently, symptoms of ANSD have been identified in nuclear family members of the probands with CCHS, though the relatives of the CCHS cases tend to manifest a milder spectrum of ANSD, with fewer symptoms and/or fewer systems than the cases [Weese-Mayer et al., 2001].

CCHS is thought to be genetic in origin based upon familial recurrence data, and genetic segregation analyses. Familial recurrence data include one report each of affected monozygotic female twins [Khalifa et al., 1988], sisters [Haddad et al., 1978], male-female sibs [Weese-Mayer et al., 1993], and male-female half sibs [Hamilton et al., 1989] with CCHS. More recently, a total of five women diagnosed with CCHS in their own childhoods have given birth to infants including two with definite CCHS, one with likely CCHS confounded by severe immaturity and bronchopulmonary dysplasia, and one with later onset CCHS [Silvestri et al., 2002; McQuitty personal communication; Sritippayawan et al., 2002]. A recent report of a child with CCHS born to a woman who had neuroblastoma as an infant [Devriendt et al., 2000] provides additional evidence for a transmitted genetic component in the phenotypic spectrum of ANSD and CCHS. Further, ANSD has been studied in a case-control family design, including families ascertained through a CCHS-affected child and families of matched controls. Segregation analysis of a quantitative ANSD trait in such families found that the best-fitting model for ANSD was codominant Mendelian inheritance of a major gene [Marazita et al., 2001]. These results support the prior hypothesis that CCHS is the most severe manifestation of a general ANS dysfunction. [Weese-Mayer et al., 1993].

Pursuit of the genetic basis for CCHS by molecular genetic analysis has been limited due to the rarity of the disease (likely fewer than 400 cases worldwide). To date, most studies have also been limited to the study of genes known to be related to Hirschsprung disease. Thus far, three discrete variants which alter a single amino acid in RET, a cell surface tyrosine kinase receptor, have been reported in three unrelated CCHS patients [Amiel et al., 1998; Sakai et al., 1998; 2001]. These alterations were also present in one or both parents for two cases. A mutation in glial cell line-derived neurotrophic factor (GDNF) was reported in another patient and his unaffected mother [Amiel et al., 1998]; a mutation in endothelin-3 was reported in a fifth patient [Bolk et al., 1996]; and a mutation in brain-derived neurotrophic factor [Weese-Mayer et al., 2002] was reported in a sixth patient with symptoms of ANSD in his father. Three other reports indicate an absence of RET mutations [Bolk et al., 1996] and RNX mutations [Amiel et al., 2002; Matera et al., 2002].

Unfortunately, the success of studies that have focused on genes known to be related to Hirschsprung disease has been limited. Although, there has been a report of heterozygous expansion mutations in a polyalanine tract within PHOX2b in 18 of 29 children with CCHS in France [Amiel et al., 2003]. The expansion mutations were determined by direct sequencing of the PHOX2b gene. As is well known in the art, direct sequencing is an arduous and time intensive task.

Accordingly there remains a need for a simple, efficient assay for helping to diagnose CCHS.

SUMMARY OF THE INVENTION

One embodiment of the invention provides a method of diagnosing or confirming idiopathic congenital central hypoventilation syndrome (CCHS) in a subject. The method can include assaying for a polyalanine repeat expansion mutation in the second polyalanine repeat of the PHOX2b gene or gene product of a subject. In other words, the method provides for determining whether the subject has a polyalanine repeat expansion mutation in the second polyalanine repeat of the PHOX2b gene or gene product. In some embodiments of assays of the invention, a polyalanine repeat 25 to 33 alanine residues in length indicates that the subject has, had or is at risk for CCHS. In some embodiments of the present methods, the assay is not performed by direct sequencing or by single strand conformation polymorphism analysis. Generally, the method identifies about 65, 70, 75, 80, 85, 90, 95, 97 percent or more of subjects having CCHS.

Another embodiment provides a method of determining whether an offspring of a subject is at risk for idiopathic congenital central hypoventilation syndrome. This method can involve determining whether the subject has a polyalanine repeat expansion mutation in the second polyalanine repeat of a PHOX2b gene or gene product, such as through an assay. In these methods, the presence of a polyalanine repeat 25 to 33 alanine residues in length indicates that the offspring of the subject is at risk for CCHS.

In the above embodiments, the methods can further include obtaining a sample from the subject that includes a nucleic acid containing the second polyalanine repeat located within exon 3 of the PHOX2b gene. In these methods, the sample can include blood, white blood cells, epithelial cells, skin, hair, fibroblasts, a tissue from an organ, amniocytes, chorionic villi, embryonic cells, polar bodies, sperm and combinations thereof as desired. These and other methods can further involve amplifying the nucleic acid containing the polyalanine repeat of the PHOX2b.

In any of the above methods, the assay or determining can include quantifying the length of the polyalanine repeat of the PHOX2b gene or gene product of the subject. In yet other embodiments, the PHOX2b gene can be directly assayed to determine whether it codes for a polyalanine mutation. In still other embodiments, the methods can be used to determine whether the gene product, e.g. the PHOX2b RNA or protein, codes for or has a polyalanine mutation.

In some of the above methods, the PHOX2b gene or gene product can be separated and the size of the PHOX2b gene or gene product can be determined by comparison against a known standard. Examples of separation techniques include chromatography techniques. Any chromatographic method that separates the gene or gene product from other components in the sample can be used in the present invention. Non-limiting examples of chromatographic methods include HPLC, dHPLC and the like. The separation can also be performed by electrophoresis.

The present methods can further include confirming whether the subject has the polyalanine mutation in the polyalanine repeat of the PHOX2b gene or gene product by sequencing the PHOX2b gene or gene product, including the polyalanine repeat region.

The present methods can be used to identify PHOX2b mutations indicative of CCHS in subjects or their offspring that have been diagnosed, at least presumptively, with sudden infant death syndrome. Some of the subjects or their offspring diagnosed by the present methods can have Hirschprung disease, alveolar hypoventilation, a tumor of neural crest origin and combinations of these diseases and disorders. In some instances, there can be a correlation between the polyalanine repeat of the PHOX2b gene or gene product and the severity of the symptoms of autonomic nervous system dysregulation characteristic of CCHS. Accordingly, the present methods can be useful for identifying therapeutic regimens for subjects having CCHS. The present methods can further include determining whether a parent of the subject has a polyalanine mutation in a polyalanine repeat of a PHOX2b gene or gene product, such as by an assay. In any of the above methods, the subject can be an embryo, fetus, child, juvenile or adult. Although the methods and assays of the present invention have special significance in the diagnosis and confirmation of fetal, infant and juvenile CCHS, the skilled artisan will understand that the methods and assays may be used to diagnose or confirm CCHS in a subject of any age. For example, the methods and assays of the present invention may be used to determine if an older infant, child, or adult, including someone over the age of one year as well as someone over the age of 20 years, has late onset central hypoventilation syndrome. Generally, if the term proband is used, it denotes the family member through whom a family's medical history comes to light. In some of the present methods, the subject is human.

The present invention also provides kits for performing the present methods.

DETAILED DESCRIPTION

Figure 1:
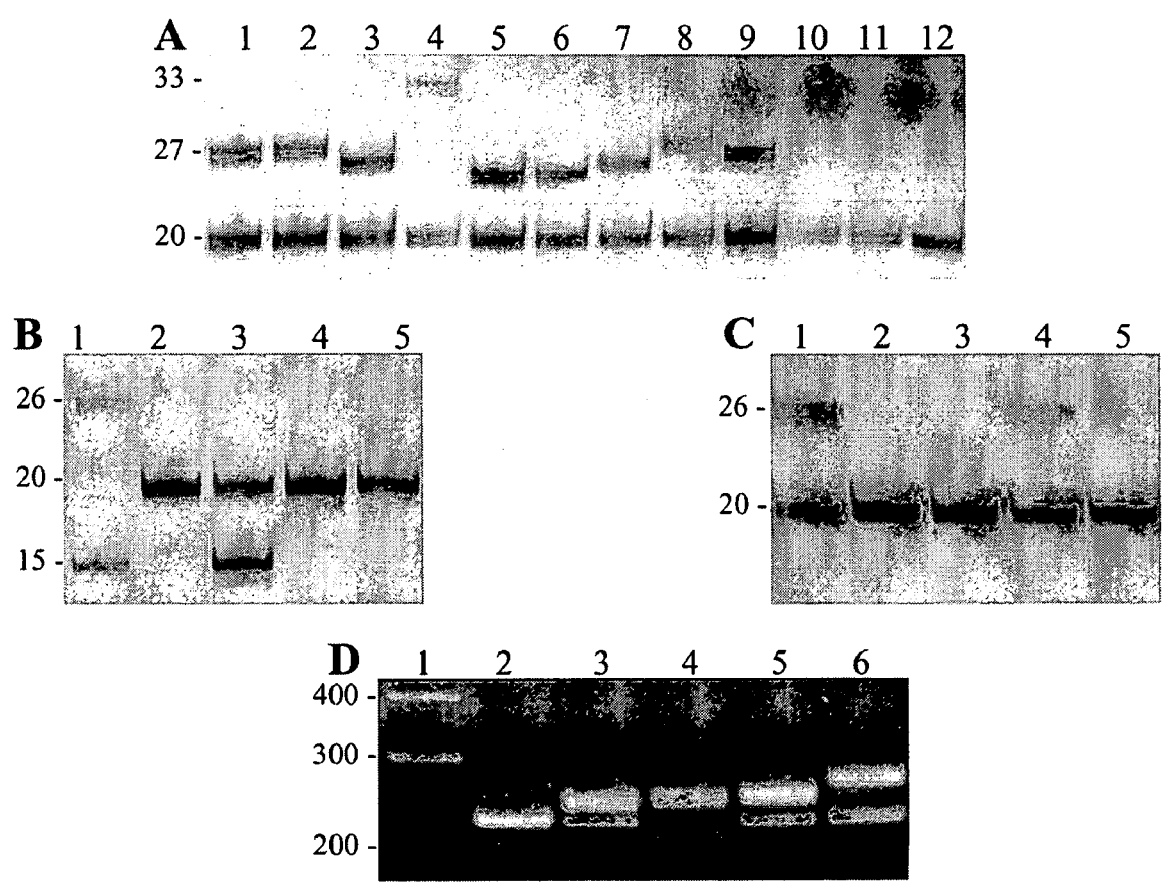
FIG. 1. Polyalanine expansion mutation in individuals and families with CCHS: (A) Polyacrylamide electrophoresis of products from CCHS subjects (lanes 1-9) and controls (lanes 10-12). Genotypes in terms of polyalanine repeat numbers are as follows: 20/27 (lanes 1, 2, 9), 20/26 (lanes 3, 7), 20/33 (lane 4), 20/25 (lanes 5, 6), 20/28 (lane 8), 20/20 (lanes 10-12). (B) CCHS mutation in family segregating deletion variant. The proband (lane 1) has alleles of 15 and 26 repeats while the father (lane 3) carries the deletion variant with 15 repeats in addition to his normal allele of 20 repeats. The mother (lane 2) and two siblings (lanes 4, 5) have only the normal 20 repeat allele. (C) CCHS proband and mother who is mosaic for expansion mutation. The proband (lane 1) has genotype 20/26 while the mother (lane 4) also has this genotype but the band intensity of the mutated 26 repeat allele is much lighter than that of the normal allele. The father (lane 2) and both maternal grandparents (lanes 3, 5) have only the normal 20 repeat allele. (D) Rapid screening for the expansion mutation by agarose electrophoresis which identifies even the smallest expansions. Molecular weight markers are in lane 1. Control with 20/20 genotype is in lane 2. Probands with CCHS expansion mutation have genotypes 20/25 (lane 3), 15/26 (lane 4) 20/27 (lane 5), and 20/33 (lane 6).

The present invention provides a method or assay for diagnosing or confirming the diagnosis of CCHS in a subject. The present methods focus on the second polyalanine repeat of the paired-like homeobox 2b (PHOX2b), protein and the nucleic acids, both DNA and RNA, that code for the protein. PHOX2b has also been referred to as NBPhox and PMX2B. Some assays determine the size of the PHOX2b exon 3 gene sequence coding for the polyalanine repeat in order to identify individuals affected with symptoms of CCHS or at risk of passing a CCHS mutation to their offspring. Other assays detect the downstream gene products, such as RNA or proteins, of the PHOX2b gene to determine the number of polyalanine repeats contained or coded for by the gene product.

PHOX2b maps to chromosome 4p12 and encodes a highly conserved homeobox domain transcription factor (314 amino acids in length), with two short and stable polyalanine repeats of 9 and 20 residues. [Amiel et al., 2003] PHOX2b has an early embryologic action on pan-neuronal differentiation including upregulation of proneural gene expression and MASH1 expression [Dubreuil et al., 2002]. PHOX2b also has a separate role by a different pathway wherein it represses expression of inhibitors of neurogenesis [Dubreuil et al., 2002]. Further, PHOX2b acts as transcriptional activator in promotion of generic neuronal differentiation and expression of motoneural differentiation [Dubreuil et al., 2002]. Finally, PHOX2b is required to express dopamine beta hydroxylase [Lo et al., 1999], RET and MASH1 as well as tyrosine hydroxylase, thereby indicating regulation of PHOX2b over the noradrenergic phenotype in vertebrates [Pattyn et al., 1999]. This role of PHOX2b early in the embryologic origin of the ANS with a role in determining the fate of early neuronal cells and a role in disinhibition of neuron differentiation might account for the seeming imbalance in the sympathetic and parasympathetic nervous system in children with CCHS.

Sequences reported for the PHOX2b gene with or without the promoter region and 5' untranslated region are disclosed as accession numbers AF117979, AB015671, BC017199, NM_008888.1 and D82344 available in the NCBI database at http://www.ncbi.nlm.nih.gov/entrez/query.fcgi.

The wild type PHOX2b cDNA has the sequence (Accession No. AF117979):

ttaaatttta attagagatg caggatcaat gatagggagt tggacagttc agttc-
ccag tgccagccca atagacggat gagttatttt catgtaaaaa gcgccag-
caa taagaccaac cgtttgttat tgtcccaagt ggaaagagcc aagtttatta
tgaggactat atggttttag agacttcaga caaggcatnt cataggaggc
tttttcataa aactaggntc tgctggtagt aaggaggcca gtttggaggc
aggcgttgag ctgtgcacat ctccccactc cagccaccct tccatatcc
atcttttatt tcattttcc acttggctga gccatccaga acctttcaa
tgtataaaat ggaatattct tacctcaatt cctctgccta cgagtcctgt atg-
gctggga tggacaccct gagcctggct tcagcctatg ctgacttcag ttcct-
gcagc caggccagtg gcttccagta taacccgata aggaccactt
tggggccac gtccggctgc ccttccctca cgccgggatc ctgcagcctg
ggcaccctca gggaccacca gagcagtccg tacgccgcag gtaaggacct
tcagctttct cagcgcagga agccgccttt ccgcccgtat ataggaagcc
ttgattgcat ttgaaaatgg aaatgtgttt agtatttacc aaacgaaatt tgctta-
caca aatgaaagaa tttatcacgt tagaagcgat tgcagggagg ggtaat-
tcac ttacagggtt acactatcct agtcacaccc gaaccgccaa caaaat-
tatc ttaagctgcc aaaatgatag gcataattta tttactttgc gatgagacgt
aaagcttaga aaataattaa ataacaaaga gtaaagctca ttactggcag
tgtctctttt tttaagaacc gacagcggct cacacctctt tggctggtca tttt-
tatgat tatttcttta atttattatt atttttttgc agctctttcc cccaactttt gagc-
cgggtc aactttctga gaattgaaaa gttcccaaag tgggactgtt tgg-
taacttc tttcctggct ccctgatatt ccgactgatg tttttggatt ttttccttct
ctggftttttt cctgctgaaa gcactatctc aagtccgtca catcgcgctg
tttcaatcca cccaaaggcg cttgtgccag aaaggactcc gccaagcccg
aagtttgagc ccaggtttcc gcagataaca aatttcctcg gtttcttccc
gcagcttctc tcggcaactc tctcgcgcgg gtgtaggtag cggctgccgt
atgacctgac cttggagtcc tcacattcta gctccacggc cggcgagctg
ccggctgatt tgctcacttt ctgtctcctc tgtcatactc tagttcctta
caaactcttc acggaccacg gcggcctcaa cgagaagcgc aagcagcgc
gcatccgcac cacttcacc agtgcccagc tcaaagagct ggaaagggtc
ttcgcggaga ctcactaccc cgacatctac actcgggagg agctggccct
gaagatcgac ctcacagagg cgcgagtcca ggtacgcgcg cctggaaacc
gaccccgctc cgccgcactg gtccggggag gtgtggggtg aggggcggct
ggtaaattcg aagtcctgga gcctcgagtg agaaggacct agggcccat
ggccgatcag aaatactgga tttggtgtgg ctgtgcgttc gagagaggct
tagagcgcac gctcttggca tttttatttac agttgcgaag tgtttccac
ccgagcagag acatggggg ccttgggacg tggatgagcg atgcaatttc
ggggacagga agtgcctgtg gtggaaggtg tgcagacttt gctcccgtat
tataagtttt tccttctccc ctcccgcccc ccaaaaaaat gcctcctaac
tcaagtgctt ttaacctgcc cccatgcat ataggttcat ttttccggaa act-
gtgactt gcatcagatt tgcaaagggt ctgtgacttc atgaaggtca agaac-
catga cttactccaa cctgttaaac acaggtgcgc tcacgagttg gcca-
cagcgc ctctctgggt gagcccccga ccgagaagcg gtgcgcacca
tcgcacgctc ttccaggctc aaaggccggg gatgggcagc ggagcaaacc
cagaggatcc ctttttccttc taccaattag agtttaactt tagaacttag gct-
tagggggt gaatggcgag ctcggggctt gctcaagaag ccgacttgaa
cagaggccca ccaaaataag gccttcccttt ttcgggtctt tctgggacct
gcggcttttt aaactctgcc gcaagccttc atgtccctgg cgtgctcact
cccctaaga aagtttctcc gaaaatgcac agcaataaga agcggtagac
ttggtggat tgcgcgcggg ggtgatcaca gcgcatgggg aggagggtgt
taaaacaagc cgaagtagaa cttgggccac cctaaccggt gcttttcttt
cccattttct tctttctccc cctgcttcac cgtctctcct tccgtcttgg gccag-
gtgtg gttccagaac cgccgcgcca agtttcgcaa gcaggagcgc
gcagcggcag ccgcagcggc cgcggccaag aacggctcct
cgggcaaaaa gtctgactct tccagggacg acgagagcaa agaggccaag
agcactgacc cggacagcac tgggggccca ggtcccaatc ccaaccccac
ccccagctgc ggggcgaatg gaggcggcgg cggcgggccc agcccg-
gctg gagctccggg ggcggcgggg cccgggggcc cgggaggcga
acccggcaag ggcggcgcag cagcagcggc ggcggccgcg gcagcg-
gcgg cggcggcagc ggcagcggcg gcagctggag gcctggctgc
ggctgggggc cctggacaag gctgggctcc cggccccggc cccatcacct
ccatcccgga ttcgcttggg ggtcccttcg gcagcgtcct atcttcgctc
caaagaccca acggtgccaa agccgcctta tgaagagca gtatgttctg
atctggaatc ctgccggcgc ggcggcggcg gcgacagcgg gcgagc-
cagg gcccggcgg gcgagtgggc gagcgggtag gcccaaggct
attgtcgcg ctgctgccat ggcttttca ttgagggcct aaagtaatcg
cgctaagaat aaagggaaaa cggcgtcgcc ctcatttcaa ccccactcct
acccccttcc tcaacccccca aacaaaacaa acaaacttcc ctggcttcgc
acctgcctgg ggcctcgcag cggggccagg gctccgcctg ctgatcgggg
gttgtgagca gcgcggcctg gacgcggggc actctcaggg ggctgtgtct
gcgtgtcagt ttgtgtctgt ctcgggggaat gtgtgtctgt ggcccaagca ggt-
gacagga agagatgggg ggcctcaacc aacttagtga cttgtttaga
aaaaaaagac aaaaaagtaa aaataaaaac aaaaaagttg gaaggcagaa
accattaaaa aacaaaaagc caacaaccca gaaaggttta aaaaacataa
ggaaaaaaaa gacaaattaa aggaggggct aggggagaag ctg-
cagctgg agctgaaggc tcgatcttgt gaacccctaa atccgctccc
tcctaacagc acggattctc ttgggggctct tcttcaggga agagtaggga
cgccgttcca gccccccttc ctatcgtgtc cttgggttcg ggtcactgcg
gcgacgactt gctcagactg tcccggcggc cggagtgact ttctcgcacc
cccttgcctg tcccacctcg ctgaacacca tcccgccatt agcgcatcgg
aaccccacac agttgcaact cccaaccccg aatctttgca gccgttcggc
cctgaaagat gccctatcca tgagatgcct tttcatctgc aaactctgca aaat-
gtgtct catgtttcgc aactctttt ttcccctcg ctccgcctcta ccccgtcggc
attttcttct tccaccagct tttactgaac ttttttggcac tgctttggat tggggt-
caat tgcagtccac gtaactggct gcagagaaat ctaccgagca
aggaaaaggc acacacacac gtttgcaggg gtgtctcggt ttgcatttct
gttggaatga tccgaactgg actcacatcc tgtatggtgg atggactgta tat-
tgagggt tccattcttc gcgcagttta gacatctctg ttttgattct ttgttgttgt
ttttatttta aaaggcacaa actctagata ttagttgaat gttgaggctt
taacttttc ggtgtctttc tacaactgtg ttctgtgact caattgtatc gtgt-
taatat cagtgcagac tgtctcctct acgtgaccgt ataatgtttt tctcgtcttg
tagtctctat ggcgtgtctt tatggtgtaa taaggttctc acggggtcaa
tctttttgtgt ttagagaggc cacggttcag acaatggtat atattttgt tatcag-
gtgc atgtctgtct gatttctttt tttttcctgt tggactatgt ttgtgaacat aat-
tgtcata agttatgttt cagatttttg aatttatttta tatgtgttat aatgaatgct
tctatttaaa agggaaatat ttctacatgt gcttatagtt ttccaagagt gtac-
cattaa cttgattgtt gataataaaa accaaaagca agtct SEQ ID NO: 1. Adachi et al., DNA Cell Biol. 19 (9), 539-554 (2000); Yokoyama et al., Genomics 59 (1), 40-50 (1999), Pattyn et al., Nature 399 (6734), 366-370 (1999); Pattyn et al., Development 124 (20), 4065-4075 (1997); and Yokoyama et al., DNA Res. 3 (5), 311-320 (1996).

The wild-type protein encoded by the PHOX2b gene in humans has the sequence (Accession No. AAD26698; corresponding amino acid sequence to Accession No. AF 117979):

mykmeysyln ssayescmag mdtsslasay adfsscsqas gfqynpirtt
   fgatsgcpsl tpgscslgtl rdhqsspyaa vpyklftdhg glnekrkqrr irt-
   tftsaql kelervfaet hypdiytree lalkidltea rvqvwfqnrr
   akfrkqeraa aaaaaakng ssgkkksdssr ddeskeakst dpdstggpgp
   npnptpscga ngggggpsp agapgaagpg gpggepgkgg
   aaaaaaaaaa aaaaaaaaaa gglaaaggpg qgwapgpgpi tsipd-
   slggp fgsvlsslqr pngakaalvk ssmf SEQ ID NO: 2. Adachi et al., DNA Cell Biol. 19 (9), 539-554 (2000); Yokoyama. et al., Genomics 59 (1), 40-50 (1999), Pattyn et al., Nature 399 (6734), 366-370 (1999); Pattyn et al., Development 124 (20), 4065-4075 (1997); and Yokoyama et al., DNA Res. 3 (5), 311-320 (1996).

The wild-type protein encoded by the PHOX2b gene in *mus musculus* has the sequence (Accession No.: NP_032914; corresponding amino acid sequence to Accession No. NM_008888.1)

mykmeysyln ssayescmag mdtsslasay adfsscsqas gfqynpirtt fgatsgcpsl tpgscslgtl rdhqsspyaa vpyklftdhg glnekrkqrr irttftsaql kelervfaet hypdiytree lalkidltea rvqvwfqnrr akfrkqeraa aaaaaakng ssgkksdssr ddeskeakst dpdstggpgp npnptpscga nggggggpsp agapgaagpg gpggepgkgg aaaaaaaaaa aaaaaaaaaa gglaaaggpg qgwapgpgpi tsipdslggp fasvlsslqr pngakaalvk ssmf SEQ ID NO: 3. Yokoyama et al., Genomics 59 (1), 40-50 (1999), and Pattyn et al., Development 124 (20), 4065-4075 (1997).

The present assays of the PHOX2b polyalanine repeat mutation can represent a highly sensitive and specific technique for confirming the diagnosis of CCHS. Identification of the CCHS mutation can further lead to clarification of the phenotype, allow for prenatal diagnosis for parents of CCHS probands and adults at risk for having children in future pregnancies with CCHS, and potentially direct intervention strategies for the treatment of CCHS.

In a specific embodiment, the present methods involve an amplification assay for diagnosis of Idiopathic Congenital Central Hypoventilation Syndrome (CCHS) by detection of polyalanine repeat expansion mutations in the PHOX2b gene. In this embodiment, a nucleic acid amplification, such as a polymerase chain reaction-based (PCR) assay is used to detect and/or determine the size of polyalanine expansion mutations in the PHOX2b gene. The amplification reaction contains nucleic acid, such as DNA or RNA, from the individual who is to be tested, and all the necessary components for amplifying the relevant portion of the nucleic acid, such as oligonucleotide primers specific for nucleic acid sequences flanking the repeat-coding area of the PHOX2b gene, nucleotides, a polymerase, salts, and buffer. The reaction mixtures are subjected to amplification, typically in a thermal cycler, and the amplification products are separated from other components of the reaction, such as by electrophoresis on a gel, so that the size of the products, which reflect the size of the gene sequence, or the gene product sequence, of the individual to be tested, can be determined. The number of repeats is determined from comparison of the amplification products with size standard, such as nucleic acids that have known sizes, including those with known repeat sizes. The assay has been used to detect an expansion mutation, or larger number of repeats, in virtually all individuals with CCHS.

In some embodiments, 7-deaza-dGTP is used in the nucleotide mix in place of some, e.g. up to 70% or more, or all dGTP to improve nucleic acid amplification and/or isolation.

In one aspect, nucleic acid amplification may be used to isolate from genomic nucleic acid a substantially pure DNA or RNA (i.e., a DNA or RNA substantially free of contaminating nucleic acids) encoding the entire PHOX2b gene or a part thereof. In some embodiments, such a DNA or RNA is at least 95% pure, more preferably at least 99% pure. In certain embodiments, any of the oligonucleotide sequences, degenerate or otherwise, that correspond to peptide sequences of PHOX2b disclosed herein can be used as primers.

The present assays can also use various probes and probing strategies that are specific for the target PHOX2b nucleic acid gene or gene product sequences to determine the number of polyalanine repeats the nucleic acids code for. In this embodiment, the assay can involve adding a probe or number of probes, such as nucleic acids specific for a given number of polyalanine repeats to a sample containing the PHOX2b sequence of interest and determining whether the probe binds to the PHOX2b nucleic acid. In one embodiment, one probe that is specific for the naturally occurring 20 alanine repeat can be used to determine whether the nucleic acid sample contains only the naturally occurring 20 polyalanine repeat or whether the nucleic acid sample also contains nucleic acids with more or less polyalanine repeats than the 20 polyalanine repeat. One or more probes that are specific for different polyalanine repeat lengths, for example 25 to 33 repeats, can additionally or alternatively be used in the assay. In the present methods, the sequence or identity of the probe(s) is (are) not particularly limited as long as the probe(s) can discriminate between the naturally occurring 20 polyalanine repeat and the polyalanine repeats that are indicative of CCHS. One skilled in the art can readily produce such probes based on the identified nucleic acid and/or protein sequence of PHOX2b. In some probe embodiments, the probes will not only have sequences complementary to those found in the polyalanine repeat coding sequence they will also have sequences, for example from three to 20 bases in length, that correspond to one or both of the sequences adjoining the polyalanine repeat coding sequence. In some embodiments, one or both of the probe(s) and target PHOX2b nucleic acid will be labeled with a detection moiety.

Specificity of the probe-target binding can be determined through any means known in the art, such as by determining the Tm of the nucleic acid complex. In some of these assays, the results can be compared against one or more control samples that contain nucleic acid with the naturally occurring 20 polyalanine repeat and/or mutants having a known number of polyalanine repeats.

Other embodiments of the present methods involve directly assaying a peptide or protein produced from the PHOX2b gene to determine the number of polyalanine repeats present in the protein. The size of the protein and number of polyalanine repeats can be determined in any suitable manner, such as by isolating the protein and/or separating the protein. As above, the size of the protein can be compared against control proteins that have known, defined sequences and sizes. The peptides or proteins may also be sequenced. The present invention also contemplates the use of antibodies, or fragments thereof, that are specific for PHOX2b proteins that have different polyalanine repeat lengths. Production of antibodies and antibody fragments specific for a target protein are well known in the art [Pattyn et al., 1997] and will not be discussed herein in detail.

Sample nucleic acid or protein to be analyzed by any known diagnostic and prognostic methods can be obtained from any cell type or tissue of a subject. For example, a subject's bodily fluid (e.g. blood) or cells can be obtained by known techniques (e.g. venipuncture, biopsy or the like). Alternatively, nucleic acid tests can be performed on dry samples (e.g. hair or skin). Fetal nucleic acid samples can be obtained from maternal blood as described in International Patent Application No. WO91/07660 (Bianchi). Alternatively, amniocytes or chorionic villi may be obtained for performing prenatal testing. The genomic DNA used for the diagnosis may be obtained from body cells, such as those present in peripheral blood, urine, saliva, buccal mucosa, surgical specimen, and/or autopsy specimens. The DNA may be used directly or may be amplified enzymatically in vitro through use of PCR (Saiki et al. Science 239:487-491 (1988)) or other in vitro amplification methods such as the ligase chain reaction (LCR) (Wu and Wallace Genomics 4:560-569 (1989)), strand displacement amplification (SDA) (Walker et al. Proc. Natl. Acad. Sci. U.S.A. 89:392-396 (1992)), and/or self-sustained sequence replication (3SR) (Fahy et al. PCR Methods Appl. 1:25-33 (1992)), prior to mutation analysis.

The methodology for preparing nucleic acids in a form that is suitable for mutation detection is well known in the art.

The detection of mutations in specific nucleic acid sequences can be accomplished by a variety of methods including, but not limited to, restriction-fragment-length-polymorphism (RFLP) detection based on allele-specific restriction-endonuclease cleavage (Kan and Dozy Lancet ii:910-912 (1978)), hybridization with allele-specific oligonucleotide probes (Wallace et al. Nucl Acids Res 6:3543-3557 (1978)), including immobilized oligonucleotides (Saiki et al. Proc. Natl. Acad. Sci. U.S.A. 86:6230-6234 (1989)) or oligonucleotide arrays (Maskos and Southern Nucl Acids Res 21:2269-2270 (1993)), allele-specific PCR (Newton et al. Nucl Acids Res 17:2503-2516 (1989)), mismatch-repair detection (MRD) (Faham and Cox Genome Res 5:474-482 (1995)), binding of MutS protein (Wagner et al. Nucl Acids Res 23:3944-3948 (1995), denaturing-gradient gel electrophoresis (DGGE) (Fisher and Lerman et al. Proc. Natl. Acad. Sci. U.S.A. 80:1579-1583 (1983)), RNAase cleavage at mismatched base-pairs (Myers et al. Science 230:1242 (1985)), chemical (Cotton et al. Proc. Natl. Acad. Sci. U.S.A. 85:4397-4401 (1988)) or enzymatic (Youil et al. Proc. Natl. Acad. Sci. U.S.A. 92:87-91 (1995)) cleavage of heteroduplex DNA, methods based on allele specific primer extension (Syvanen et al. Genomics 8:684-692 (1990)), genetic bit analysis (GBA) (Nikiforov et al. Nucl Acids Res 22:4167-4175 (1994)), the oligonucleotide-ligation assay (OLA) (Landegren et al. Science 241:1077 (1988)), the allele-specific ligation chain reaction (LCR) (Barrany Proc. Natl. Acad. Sci. U.S.A. 88:189-193 (1991)), gap-LCR (Abravaya et al. Nucl Acids Res 23:675-682 (1995)), and radioactive and/or fluorescent nucleic acid sequencing or labeling using standard procedures well known in the art.

Diagnostic procedures may also be performed in situ directly upon tissue sections (fixed and/or frozen) of subject tissue obtained from biopsies or resections, such that no nucleic acid or protein purification is necessary. Nucleic acid reagents may be used as probes and/or primers for such in situ procedures (see, for example, Nuovo, G. J., 1992, PCR in situ hybridization: protocols and applications, Raven Press, N.Y.).

As used herein, a gene product or product of a gene refers to a molecule that is produced based on the sequence of the gene. Examples of gene products include RNA, such as mRNA, and proteins.

PHOX2b analyses in the present examples were also extended to parents and other family members of CCHS cases, and parent/infant pairs in which the mother had CCHS. The PHOX2b assays in the examples were specifically undertaken to develop a simple and accurate assay for sizing of the repeat sequence associated with the polyalanine tract expansion, and clarify inheritance patterns for CCHS mutations in families.

In the methods and assays embodied in the examples, 65/67 CCHS probands (97%) were found to be heterozygous for the exon 3 polyalanine expansion mutation of PHOX2b. Further, there was an association between repeat mutation length and severity of the CCHS/ANSD phenotype. Of the two probands who did not carry the expansion mutation, one had a nonsense mutation in exon 3 that truncated the protein and the other had no mutation in PHOX2b but had a previously reported endothelin 3 (EDN3) frameshift point mutation. The polyalanine expansion mutation was not found in any of 67 matched controls. Of clinically unaffected (no CCHS) parents from 54 available families (43 parent pairs and 11 single parents) whose child carried the PHOX2b mutation in the example, four parents from the 43 parent pairs demonstrated mosaicism for an expansion mutation identical to that seen in the CCHS cases, suggesting that not all mutations in affected probands with unaffected parents are de novo. Four women with CCHS who were heterozygous for the PHOX2b mutation, each with one child, were also studied. Three of the four children were also affected and had the same mutation, demonstrating autosomal dominant inheritance of the mutation.

Based on certain embodiments of the present assays, demonstrated by the examples, PHOX2b was found to have a statistically significant association with CCHS. It appears that children with CCHS are heterozygous for a polyalanine expansion mutation in PHOX2b. The results set forth in the examples suggest that heterozygosity for a mutation in PHOX2b is sufficient to produce CCHS. The results of the methods and assays of the examples demonstrate the finding of unique PHOX2b mutations in some patients with the triad of Hirschsprung disease, alveolar hypoventilation, and neuroblastoma. Although the mutations identified were not identical, it is of great interest nonetheless, with the only other unique mutation found in one French study patient with Hirschsprung disease and alveolar hypoventilation. These observations indicate the importance of PHOX2b gene sequencing in patients believed to carry the CCHS phenotype but who do not have the polyalanine repeat mutation.

Surprisingly and unexpectedly, as shown by the results of the examples, embodiments of the present methods and assay provided a much higher success rate in identifying patients with CCHS than previous references. As can be seen from the examples, the present assay identified the PHOX2b polyalanine expansion mutation in 97% of cases and any PHOX2b mutation in 98.5% of CCHS cases, whereas prior experiments only identified 62% and 69% of patients with the PHOX2b polyalanine expansion mutation or any PHOX2b mutation, respectively. Accordingly, the present methods can specifically exclude techniques such as direct sequencing of nucleic acids and/or single strand conformation polymorphism analysis. Additionally or alternatively, the present invention also provides an assay that identifies about 65, 70, 75, 80, 85, 90, 95, 97 percent or more of subjects that have, or are at risk for, CCHS.

Embodiments of the invention allow determination of an association between PHOX2b polyalanine repeat mutation length and severity, as measured by numbers of ANSD symptoms and daily duration of required ventilatory support. This determination was surprising and unexpected.

Additionally, using individual embodiments and methods of the present invention, the present inventors have discovered that offspring of a subject are at higher risk for CCHS when the subject has a polyalanine expansion mutation, for example where the subject is a somatic mosaic for the polyalanine expansion mutation. This is in contrast to previous studies that did not identify PHOX2b polyalanine repeat mutations in parents of CCHS probands, but instead suggested that the mutation arises as a de novo event in subjects with CCHS. As demonstrated in the examples, the present methods and assays did find a polyalanine repeat mutation, apparently present as a somatic mosaic, in 4 asymptomatic (for CCHS) parents, suggesting that in a small (~10%) percent of families with a child with CCHS, there is a risk of recurrence in a second child. The finding of the mosaic carrier parents is consistent with prior reports of sibships with CCHS [Haddad et al., 1973; Hamilton et al., 1989; Khalifa et al., 1988; Weese-Mayer et al., 1993]. Parental mutation screening is therefore important after identification of a child with CCHS and a PHOX2b mutation, in order to provide appropriate counseling to the family regarding recurrence risk.

Given that somatic mosaicism exists in some families, it is possible that germline mosaicism also exists; after birth of a child with CCHS, prenatal testing should be performed to predict the affection status of subsequent pregnancies. Only the embodiments of the present invention are known to be sensitive enough to provide this screening.

Transmission of CCHS from parents with CCHS to their children was addressed through the study of four mother-child pairs in which the mother had CCHS and the PHOX2b polyalanine expansion mutation. In these cases, the mutation and the disease were transmitted in an autosomal dominant fashion: inheritance of one copy of the expanded allele resulted in disease, while inheritance of the normal 20 repeat allele (from both parents) did not result in disease. One of the affected children was initially considered to be asymptomatic, but prior to determining that he was carrying the PHOX2b mutation he became ventilator-dependent during sleep after a viral illness. This observation suggests that presence of the PHOX2b expansion mutation as demonstrated by using the methods and assays of the invention is highly predictive of disease, even in an infant not initially showing signs of CCHS. As shown in the embodiments of the examples, in all three cases in which the expansion mutation was transmitted from mother to child, there was no change in the number of repeats and mother and child carried the same alleles. Likewise, in all four cases where a CCHS parent was a mosaic, the expansion mutation was transmitted parent to child with no change in the number of repeats and the mosaic CCHS parent and CCHS proband child carried the same alleles. The results from this group suggest that the polyalanine expansion in PHOX2b is meiotically stable. In combination with the notable absence of the 1-4 repeat expansions in control and CCHS groups, these results support that the mutation is likely to occur through mispairing during replication followed by unequal crossing over rather than through a strand slippage mechanism. However, the skilled artisan will understand that embodiments of the invention may work through separate mechanisms.

Extensive studies by Pattyn et al. [1997, 1999] indicate an early expression pattern of PHOX2b in rhombencephalon, suggesting a link to early patterning events with later neurogenesis in the hindbrain. In the mouse, PHOX2b is expressed in the neonatal CNS, specifically in the area postrema, nucleus tractus solitarius, dorsal motor nucleus of the vagus, nucleus ambiguus, ventral surface of medulla, locus coeruleus (until embryonic day 11.5), and the IIIrd (oculomotor), IVth (trochlear), VIIth (facial), IXth (glossopharygeal), and Xth (vagus) cranial nerves. Until midgestation in the mouse, PHOX2b is expressed in the Vth (trigeminal) cranial nerve. In the mouse peripheral nervous system, PHOX2b is expressed in the distal VIth, IXth and Xth cranial sensory ganglia from embryonic day 9.5 and in all autonomic nervous system ganglia as early as formed, until at least midgestation. Finally, by embryonic day 9-9.5, PHOX2b protein is detected in enteric neuroblasts invading the foregut mesenchyme; with expression in the esophagus, small intestine, and large intestine. In the PHOX2b knock-out, the gut is devoid of enteric neurons and even the neural crest-derived cells that are found in the foregut at E10.5 do not survive or migrate [Young et al., 1999]. Recognizing the phenotype of CCHS with symptoms of ANSD in the respiratory control system (100% of CCHS probands), cardiovascular system (90% of CCHS probands), ophthalmologic system (88% of CCHS probands), neurological system (53% of probands), and gastrointestinal system (96% of probands) among subjects tested in the present examples, these findings follow logically from the embryologic distribution of PHOX2b. It remains unclear how the distribution and actions of PHOX2b account for involvement of other systems often included in the ANSD profile of the child with CCHS, including the sudomotor system (80% of CCHS probands), psychological system (30% of CCHS probands), and the renal system (29% of CCHS probands).

Polyalanine expansion mutations have been described as a cause of disease in a number of homeodomain- and non-homeodomain-containing transcription factors including HOXD13 (synpolydactyly), HOXA13 (hand-foot-genital syndrome), RUNX2 (cleidocranial dysplasia) and ZIC2 (holoprosencephaly) [Goodman and Scambler, 2001]. There is precedent for polyalanine repeat tract expansion in a homeobox gene as a cause of neurological disease due to presumed failure of specification and/or migration of a specific neuronal cell type. The Aristaless-related homeobox gene (ARX) gene has been associated with XLAG (X-linked lissencephaly and ambiguous genitalia) [Kitamura et al., 2002], X-linked mental retardation [Bienvenu et al., 2002], X-linked and sporadic infantile spasms, and other developmental disorders with mental retardation and epilepsy [Stromme et al., 2002]. This ARX gene contains a polyalanine tract which is expanded in some affected subjects, particularly those with infantile spasms or myoclonic epilepsy. Other subjects have missense or truncating mutations which likely result in loss-of-function. Mice with mutations in ARX show aberrant differentiation and migration of GABA-ergic neurons in neocortex [Kitamura et al., 2002]. Given the expression patterns of PHOX2b in central autonomic structures and peripheral neural crest derivatives and the wide range of ANS dysfunction seen in CCHS, there may be a similar mechanism of aberrant differentiation and/or migration of central and peripheral noradrenergic sympathetic and parasympathetic neurons results from the polyalanine tract expansion in PHOX2b. Nevertheless, one of skill in the art will understand that other mechanisms may be important in the ANS dysfunction seen in CCHS.

Without limiting the scope of the invention, the identification of mutations in PHOX2b which cause typical CCHS and produce a very truncated protein or a highly disrupted protein due to out-of-frame intragenic deletion suggests that the polyalanine expansion mutation results in CCHS through a loss-of-function mechanism. However, no mutations which disrupt the homeodomain have thus far been identified, raising the possibility that if these very abnormal proteins are stable, they may still have some function. Indeed, polyalanine expansion mutations in HOXD13 and RUNX2 are thought to cause disease through gain-of-function mechanisms. Polyalanine tracts are thought to act as spacers or protein-binding elements. Therefore, expansions of these tracts in a mutant protein which can still bind DNA could prevent normal protein interactions (loss-of-function) or allow aberrant interactions (gain-of-function) while blocking function of the normal protein coded by the non-mutated gene. This could explain the dominant inheritance pattern in a loss-of-function mutant. Further, in these models, longer repeat tracts might be expected to produce a more pronounced molecular disturbance, resulting in increasing severity and number of clinical symptoms with increased length of repeat tract, as observed in the present examples.

Clinically, evaluation of the PHOX2b expansion can be used as a predictive test for CCHS. Given that 65/67 cases and 0/67 controls in the examples were heterozygous for the PHOX2b expansion, the sensitivity is ~97.06%, with a specificity 100% when using individual embodiments of the methods and assays of the invention. Such tests could be particularly useful for parents of a child with CCHS seeking recurrence risk estimation or prenatal diagnosis, for grown children with CCHS seeking pre-conception or prenatal diagnosis, and for differential diagnosis for children with seemingly confounding symptoms such as asphyxia, prematurity, bronchopulmonary dysplasia, and more. Further, a better understanding of the nature of the mutation may lead to improved treatment options for children with CCHS.

The results from the present examples are important at several levels. First, the study design serves as a paradigm of phenotypic features directing selection of candidate genes. Specifically, the symptoms of ANSD in the children with CCHS (and their relatives) motivated the study of genes which play a role in early embryologic development of the ANS. This study design therefore has applicability to other seemingly complex diseases that appear to be genetic in origin. Second, these results confirm that children with CCHS are heterozygous for a PHOX2b polyalanine expansion mutation. The identification of this mutation in most individuals with CCHS allows a definitive confirmatory test for infants suspected to have CCHS and allows for diagnostic homogeneity in CCHS cohorts used for research studies. Third, because the family studies presented in the examples are consistent with an autosomal dominant pattern of inheritance for CCHS, certain embodiments of the invention allow for careful informed pregnancy planning for families of CCHS cases.

It will be understood to those skilled in the art that the present invention readily lends itself to automation. As an automated process, several samples containing the same, or different, combinations of nucleic acids and/or proteins can be assayed in parallel.

The present invention also provides kits for carrying out the methods described herein. In one embodiment, the kit is made up of instructions for carrying out any of the methods described herein. The instructions can be provided in any intelligible form through a tangible medium, such as printed on paper, computer readable media, or the like. The present kits can also include one or more reagents, buffers, hybridization media, nucleic acids, primers, nucleotides, probes, molecular weight markers, enzymes, solid supports, databases, computer programs for calculating dispensation orders and/or disposable lab equipment, such as multi-well plates, in order to readily facilitate implementation of the present methods. Enzymes that can be included in the present kits include nucleotide polymerases and the like. Solid supports can include beads and the like whereas molecular weight markers can include conjugatable markers, for example biotin and streptavidin or the like. Examples of preferred kit components can be found in the description above and in the following examples.

Some kits will include nucleic acid primers for amplifying the PHOX2b nucleic acids. Kits can also contain probes specific for the PHOX2b gene and gene products as described herein.

EXAMPLES

Study Subjects. Four distinct groups were investigated in this study, including CCHS probands, gender- and ethnicity matched controls, parents and other relatives of CCHS probands, and CCHS parent/infant pairs. For all subjects, ethnicity was assigned based on self-report. This study was approved by the Rush University Medical Center institutional review board and informed consent was obtained from all subjects and their parents or legal guardians.

CCHS Cases. Sixty-nine CCHS probands (age range at enrollment 2 months to 22 years) with a diagnosis made by study in the Respiratory Physiology Laboratory at Rush Children's Hospital and/or following thorough review of the medical records (DEW-M) were enrolled in the study. The diagnosis of CCHS was based on the accepted definition in the American Thoracic Society Statement on the diagnosis and management of Idiopathic CCHS. [Weese-Mayer et al., 1999]. Because DNA was not obtainable from 2 of the deceased children with CCHS, 67 CCHS probands were included in the genetic studies.

Control Subjects. Sixty-seven unrelated control subjects were matched for ethnicity and gender to the CCHS cases with a 1:1 match ratio (collected at Rush Children's Hospital, Chicago, Ill.). After informed consent was obtained, a three-generation family history was taken for each control to ensure that no family member had a diagnosis of SIDS, Hirschsprung Disease, Idiopathic Congenital Central Hypoventilation Syndrome, apparent life threatening event, primary (non-acquired) disorder of autonomic nervous system (ANS) dysregulation, or tumor of neural crest origin.

Parents and Other Relatives of CCHS Cases. A total of 97 parents were enrolled, including 43 sets of parents and 11 single parents (10 mothers, 1 father), whose children were diagnosed with CCHS. Parents were not available for 6 of the 7 adopted CCHS cases, or for the 4 CCHS mothers. A total of 30 siblings (20 sisters, 10 brothers), 6 half-sibs (2 half-sisters, 4 half-brothers), 7 grandparents (5 grandmothers, 2 grandfathers), 1 aunt and 2 cousins were enrolled. Analyses on parents and other relatives were limited to the PHOX2b gene polyalanine repeat mutation.

CCHS Cases with Offspring. A total of four parent/infant pairs in which the mother had CCHS were enrolled. Fathers for two of the infants were also enrolled.

Subject Population Demographics. The matched sample dataset included 67 CCHS probands and 67 matched controls with the following distribution of case-control pairs: 30 Caucasian females, 28 Caucasian males, 3 African-American females, 2 African-American male pairs, 2 Hispanic females, 1 Hispanic male, and 1 Native American Indian female. The participating parents of CCHS cases were all Caucasian with the exception of 3 African American parents (1 couple and 1 single mother), and 3 Hispanic parents (1 couple and 1 single mother). The CCHS case/offspring pairs included 1 Native American Indian (infant female), 2 Caucasian (infant males), and 1 African American (infant male).

Among the children considered to have CCHS, 9 had unique diagnoses of cerebral arteriovenous malformation [Mukhopadhyay and Wilkinson, 1990], cystic fibrosis, Tourette's, pervasive developmental delay (n=2), symptom manifestation after an acute infection (n=2), bronchopulmonary dysplasia, and brainstem hypoplasia. Among these 9 children, the secondary diagnosis had clouded the presumptive diagnosis of CCHS.

DNA Preparation. Blood (3-10 cc) was obtained by venipuncture and collected into an EDTA tube from CCHS cases and family members. Blood or a buccal swab was obtained from control subjects. Genomic DNA was isolated utilizing a Puregene reagent kit (Gentra, Minneapolis, Minn.) according to the manufacturer's instructions. DNA samples were saved in Tris-EDTA hydration buffer at −80° C. prior to genotyping. For two of the CCHS cases who had died several years earlier, paraffin-embedded rectal biopsy specimens were obtained. Despite efforts to extract DNA from these specimens, this was not achieved.

Genotyping of PHOX2b Polyalanine Repeat Sequence. The PHOX2b exon 3 region coding for the polyalanine repeat was amplified with primer pair 5'-CCAGGTCCCAATC-CCAAC-3' (forward) (SEQ ID NO: 4) and 5'-GAGC-CCAGCCTTGTCCAG-3' (reverse) (SEQ ID NO: 5) in a Perkin Elmer 9600 thermal cycler (Applied Biosystems, Foster City, Calif.). The PCR reactions were carried out using 0.25 units AmpliTaq Gold polymerase (Applied Biosystems, Foster City, Calif.) in a total volume of 25 µl containing 50 ng genomic DNA, 0.3 µM primers, 2.5 mM $MgCl_2$, AmpliTaq Gold PCR Buffer and 0.2 mM dNTPs with 70% 7-deazaGTP, 0.2 uCi of ($^{32}$P)dCTP (Perkin Elmer/NEN Life Sciences, Boston, Mass.) and 10% glycerol. The amplification was performed with an initial denaturation at 95° C. for 10 min. followed by 35 cycles of denaturation at 94° C. for 30 sec., annealing at 57° C. for 30 sec. and extension at 72° C. for 30 sec. Final extension was at 72° C. for 10 min. The PCR products (232 bp for normal 20 repeat allele) were subjected to electrophoresis on a 6% denaturing polyacrylamide gel, and visualized by autoradiography. Allele repeat number was determined by comparison of bands to known size standards for which repeat number had been determined by sequence analysis.

Sequence Analysis of PHOX2b. PHOX2b exons 1, 2 and 3 were amplified with primer pairs [Garcia-Barceló et al., 2003] noted in Table I to give products of 586 bp (exon 1), 442 bp (exon 2) and 687 bp (exon 3) utilizing a Perkin Elmer 9600 thermal cycler (Applied Biosystems, Foster City, Calif.). The PCR reactions were carried out using 1.25 units AmpliTaq Gold polymerase (Applied Biosystems, Foster City, Calif.) in a total volume of 25 µl containing 50 ng genomic DNA, 0.5 µM primers, 1 mM $MgCl_2$, AmpliTaq Gold PCR Buffer and 0.2 mM dNTPs. Due to its high GC content, amplification of exon 3 was performed using the GC-RICH System (Roche Molecular Biochemicals, Indianapolis, Ind.). Exon 3 PCR was performed in a volume of 25 µl containing 50 ng genomic DNA, 0.2 mM dNTPs, 5 µl of 5×GC-RICH PCR reaction buffer, 2.5 µl of 5M GC-RICH resolution solution, 0.5 µM of each primer, and 1.25 U of Taq DNA Polymerase mixture. The amplification for all 3 exons was performed with an initial denaturation at 95° C. for 8 min. followed by 35 cycles of denaturation at 95° C. for 1 min., annealing at 62° C. for 1 min., and extension at 72° C. for 45 sec. Final extension was at 72° C. for 10 min. The PCR products were column-purified with a MinElute PCR Purification Kit (QIAGEN Inc., Valencia, Calif.) to remove reaction buffer and unincorporated primers, and visualized by running 5 µl of each sample on 2% agarose gels. PCR products were sequenced on an ABI 3100 automated sequencer (Research Resource Center, University of Illinois at Chicago, Chicago, Ill.). The exon 3 reaction with the GC-Rich System was run using the primer pair flanking the polyalanine repeat (provided in section above) and products were run on a 2% agarose gel for rapid screening for presence of a repeat expansion (FIG. 1). Polyacrylamide gel electrophoresis was necessary for accurate sizing of mutations identified.

Statistical Analysis. Association between the number of PHOX2b polyalanine repeats and the quantitative traits (number of ANSD symptoms and number of affected systems as described in Weese-Mayer et al., 2001) was analyzed using a measured genotype approach [Boerwinkle et al., 1986; Boerwinkle et al., 1987]. Measured genotype analysis (MGA) consists of comparing the genotypic means by analysis of variance (ANOVA). Association between the number of polyalanine repeats and the qualitative trait "daily duration of required ventilatory support" was assessed using $\chi 2$ contingency table tests. To address the issue of a sparse contingency table, Monte Carlo tests of association as implemented in computer algorithm CLUMP were used [Sham and Curtis, 1995].

Results

Description of CCHS Matched Cohort. From the matched dataset, 12 of the CCHS cases had Hirschsprung Disease in addition to the 2 deceased children from whom DNA was not obtainable (14 of 69 CCHS cases; 20%). Three of the CCHS cases had a tumor of neural crest origin (2 with ganglioneuroma, 1 with neuroblastoma) in addition to one of the 2 deceased children with CCHS who had a neuroblastoma (4 of 69 CCHS cases; 5.8%). 54% of the CCHS cases required ventilatory support awake and asleep and 46% required ventilatory support during sleep only. Using the published list of ANSD symptoms in CCHS [Weese-Mayer et al., 2001], it was determined that CCHS cases had a predominance of symptoms of ANSD with a mean number of symptoms per subject of 9.17 (3.70) (range 3-20) and a mean number of systems involved per subject of 5.10 (1.32) (range 2-8). Among the CCHS cases, system involvement included 90% with cardiovascular, 96% with gastrointestinal, 53% with neurological, 88% with ophthalmologic, 29% with psychological, 17% with renal/urological, 100% with respiratory, and 80% with sudomotor.

Figure 2:
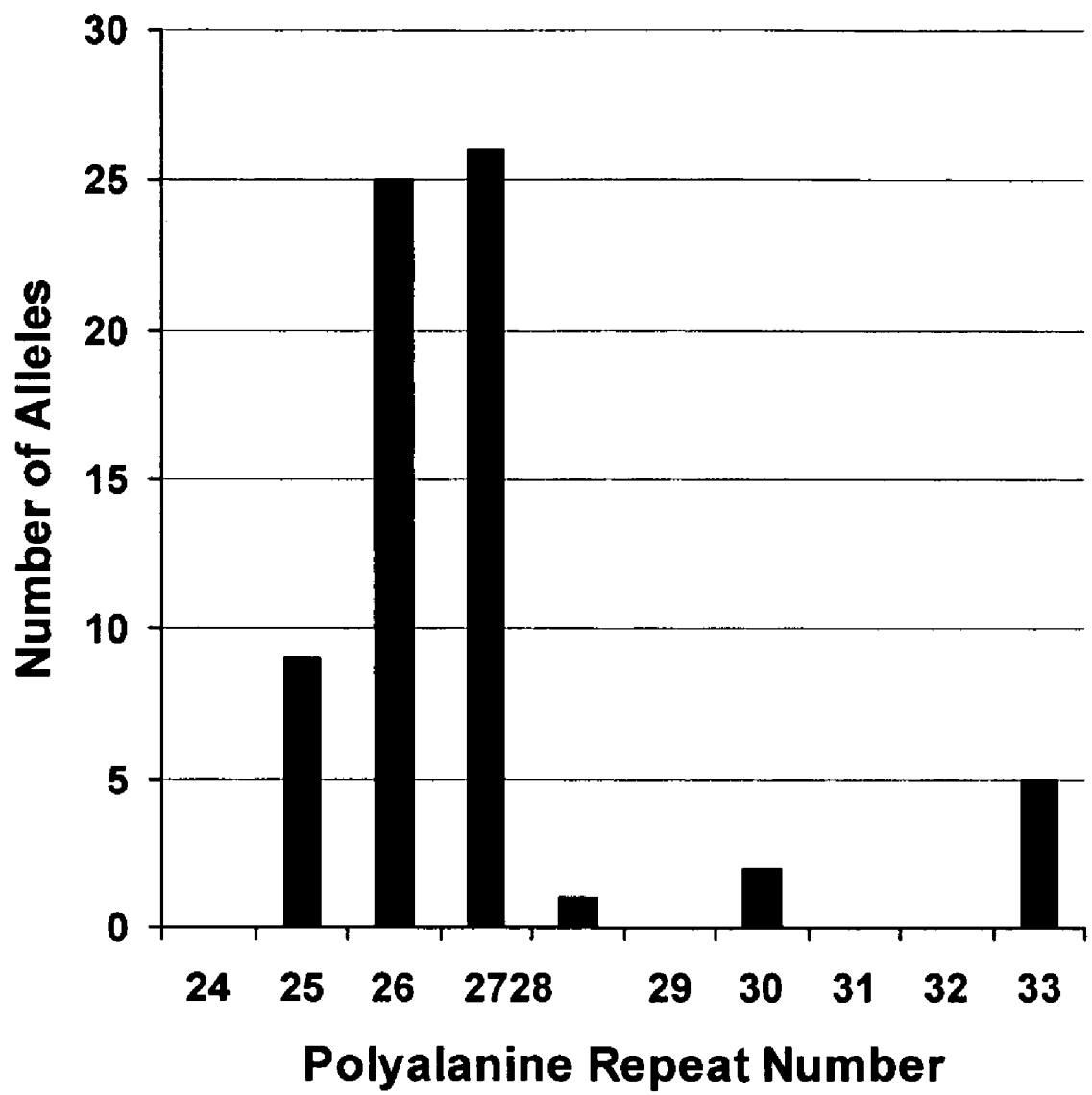
FIG. 2. Allele frequency distribution of PHOX2b polyalanine repeat expansion mutations in 65 CCHS probands and 3 infants with CCHS born to CCHS probands. Among the 13 cases with Hirschsprung disease and/or a tumor of neural crest origin as well as the polyalanine repeat expansion mutation, 5 cases (38%) have the longest polyalanine repeats (8-13). The 2 children with ganglioneuromas have the 13 repeat; 3 children with Hirschsprung disease have 13, 10, and 8 repeats.

Directed Mutation Analysis of Polyalanine Repeat Sequence in PHOX2b in Probands with CCHS. A polyalanine repeat expansion mutation was identified in 65 of the 67 (97%) probands with CCHS for whom DNA was available for analysis. All affected individuals with CCHS were heterozygous for the mutation and carried a normal allele as well as the expanded allele (FIG. 1). Expanded alleles contained insertions of 15-39 nucleotides, increasing the normal polyalanine repeat present in PHOX2b from 20 alanines to 25-33 alanines (FIGS. 1, 2). Size of the expansion mutation was confirmed by direct sequencing for seven CCHS proband samples with different repeat sizes; the inserted sequence was identified as additional alanine codons added in-frame to the 3' end of the polyalanine coding tract. The majority of expanded alleles contained 25-27 polyalanine repeats but some were larger (FIG. 2). No controls carried an expanded sequence, although two out of 67 controls were heterozygous for two deleted variants containing 15 repeats. This deletion variant was identified previously in the control population by Amiel et al. [2003], in a study where two out of 125 controls heterozygous for deleted variants containing 14 or 15 repeats.

PHOX2b Polyalanine Repeat Analysis in Parents and Other Relatives of CCHS Cases. To determine if the repeat expansion mutation is inherited and to clarify recurrence risk, 43 sets of parents and 11 single parents whose children dem-

TABLE I

| | | | |
|---|---|---|---|
| 1 GACCTCAGACAAGGCATCTCA | (SEQ ID 6) | AATTACCCCTCCCTGCAATC | (SEQ ID 7) |
| 2 CTGCCGTATGACCTGACCTT | (SEQ ID 8) | ACAGCCACACCAAATCCAGT | (SEQ ID 9) |
| 3 ACCCTAACCGGTGCTTTTCT | (SEQ ID 10) | ACAATAGCCTTGGGCCTACC | (SEQ ID 11) | onstrated the CCHS phenotype and for whom DNA was available for analysis were studied. Most parents were homozygous for the normal 20-repeat allele suggesting that most CCHS expansion mutations in the probands arose de novo. Four clinically unaffected (no CCHS) unrelated parents (representing 10% of families from which both parents' DNA was available), however, did show an expansion mutation which was identical to that seen in the affected child. The expansion mutation in all four parents of probands showed a substantially lighter signal than that seen in the normal allele, in contrast to the pattern seen in subjects with CCHS, in whom the normal allele and expanded allele had similar signal intensity (FIG. 1). This suggests that these unaffected parents are most likely somatic mosaics for the expansion mutation. Three additional unrelated parents (of the 97 total) were heterozygous for the deletion variant (2 with 15 repeats, 1 with 14 repeats) seen in the normal population and thus, the frequency of this variant was essentially the same in parents of CCHS probands as in the general population (allele frequency 0.015 in both control and parent groups). One child with CCHS inherited the deletion variant from his father in addition to an expansion mutation, presumably from the mother (FIG. 1). All other relatives studied were homozygous for the normal 20-repeat allele.

Figure 3:
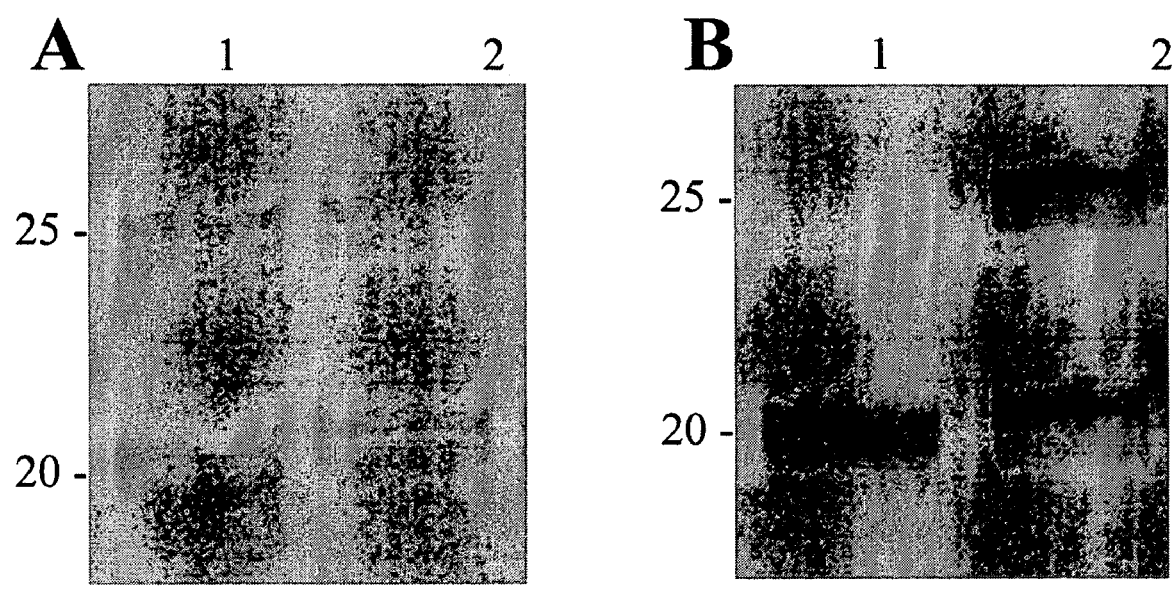
FIG. 3. PHOX2b polyalanine repeat expansion mutation in CCHS probands and their offspring: (A) mother (lane 1) and child (lane 2) both with expansion mutation (genotype 20/25) and CCHS; (B) mother (lane 2) with expansion mutation (20/25) and CCHS and child (lane 1) with normal genotype (20/20) and no symptoms of CCHS.

PHOX2b Polyalanine Repeat Analysis in CCHS Probands with Offspring. The PHOX2b expansion mutation was present in all four CCHS female probands, who were mothers of one child each. Two of these infants had symptoms compatible with CCHS in early infancy, one did not demonstrate nocturnal ventilatory dependence until after an acute respiratory infection, and one did not manifest any symptoms compatible with CCHS. The three symptomatic children were heterozygous for an expansion mutation identical in size to that seen in the mother (FIG. 3). The child with no symptoms had a normal genotype and had inherited the mother's normal allele (FIG. 3). These mother-child pairs confirm the expected autosomal dominant inheritance pattern for individuals affected with CCHS and suggest that repeat instability when the expansion mutation is passed from parent to child is not common. The two fathers who were tested demonstrated the normal 20-repeat pattern.

PHOX2b Sequence Analysis in CCHS Probands with No Polyalanine Expansion Mutation. Two children with an established diagnosis of CCHS did not show the expansion mutation. Sequence analysis of the full coding region of PHOX2b including intron-exon boundaries identified a heterozygous nonsense mutation (A463T) in one of these probands diagnosed with CCHS, Hirschsprung disease, and neuroblastoma. This mutation introduces a stop codon at K155 and is expected to produce a truncated protein which is missing most of exon 3 and the entire polyalanine tract. The other proband showed a single base change in exon 3 (G875C) which resulted in a substitution of alanine for glycine (G292A); this change was also found in one control subject. Thus, this one CCHS proband did not show any significant abnormality in PHOX2b. However, he had an atypical clinical picture with reported brainstem hypoplasia and severe mental retardation in addition to his very characteristic picture of ANSD; further, he had a previously reported EDN3 frameshift point mutation [Bolk et al., 1996].

Figure 4:
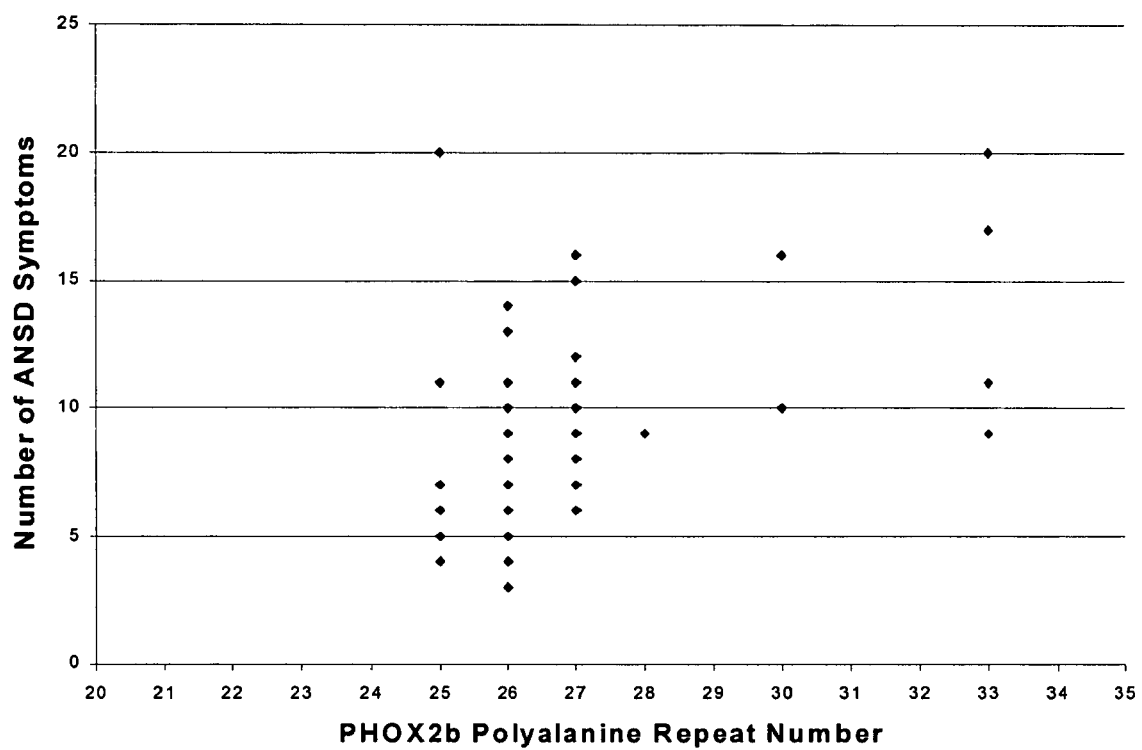
FIG. 4. Number of ANSD symptoms in CCHS probands vs. PHOX2b polyalanine repeat expansion mutation length. Many subjects had identical numbers for ANSD symptoms and polyalanine repeats, therefore the figure gives the illusion of fewer data points than expected for the 65 CCHS cases with the PHOX2b mutation.

Relationship of Polyalanine Repeats to ANSD Phenotype in CCHS Cases. Measured genotype analysis revealed a significant association between PHOX2b polyalanine repeat mutation length and number of ANSD symptoms ($F=2.93$, $df=5$, $p=0.021$; FIG. 4), but not number of ANSD-affected systems involved ($F=1.80$, $df=5$, $p=0.129$). There was also a significant association between the distribution of repeat mutation length and daily duration of required ventilatory support ($Ti=17.667$, $p=0.0034$; Table II).

TABLE II

Frequency Distribution of PHOX2b Polyalanine Repeats by Daily Duration of Ventilatory Support*

| | Number of PHOX2b Polyalanine Repeats** | | | | | |
|---|---|---|---|---|---|---|
| | 25 | 26 | 27 | 28 | 30 | 33 |
| 24 hours | 0 | 16 | 14 | 0 | 2 | 1 |
| 12 hours | 8 | 7 | 8 | 1 | 0 | 4 |

*Because the daily duration of ventilatory support was unknown for 4 CCHS probands, and 2 probands did not demonstrate the PHOX2b polyalanine expansion mutation, the total number of subjects in this table is 61. Also, decisions about daily duration of ventilatory support were made by the referring pulmonologist. In the four cases with 12 hour/day support and the 13 additional repeats (33 total polyalanine repeats), review of the medical records (performed independent of the genetic testing results) indicates markedly elevated awake carbon dioxide values and an absence of any current awake physiologic evaluations; by Rush laboratory criteria review of records, 24 hour/day ventilatory support would have been recommended to 3 of these 4 children with the 13 additional repeats.
**$P = 0.0034$ for difference in allele distribution.

The present compositions can have any or all of the components described herein, including but not limited to primers, samples, and the like. Likewise, the present methods can be carried out by performing any of the steps described herein, either alone or in various combinations. One skilled in the art will recognize that all embodiments of the present invention are capable of use with all other appropriate embodiments of the invention described herein. Additionally, one skilled in the art will realize that the present invention also encompasses variations of the present probes, configurations and methods that specifically exclude one or more of the components or steps described herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references, patents and publications disclosed herein are specifically incorporated by reference thereto. Unless otherwise specified, "a" or "an" means "one or more".

The following references, some of which are discussed herein, are specifically incorporated into the present application by reference:

Amiel J, Laudier B, Attié-Bitach T, Trang H, de Pontual L, Gener B, Trochet D, Etchevers H, Ray P, Simonneau M, Vekemans M, Munnich A, Gaultier C, Lyonnet S. 2003. Polyalanine expansion and frameshift mutations of the paired-like homeobox gene PHOX2b in congenital central hypoventilation syndrome. Nature Genetics 33:459-461.

Amiel J, Pelet A, Trang H, de Pontual L, Simonneau M, Munnich A, Gaultier C, Lyonnet S. 2003. Exclusion of RNX as a major gene in congenital central hypoventilation syndrome. Am J Med Genet 117A: 18-20.

Amiel J, Salomon R, Attie T, Pelet A, Trang H, Mokhtari M, Gaultier C, Munnich A, Lyonnet S. 1998. Mutations of the RET-GDNF signaling pathway in Ondine's curse. Am J Hum Genet 62:715-717.

Bienvenu T, Poirier K, Friocourt G, Bahi N, Beaumont D, Fauchereau F, Ben Jeema L, Zemni R, Vinet M C, Francis F, Couvert P, Gomot M, Moraine C, van Bokhoven H, Kalscheuer V, Frints S, Gecz J, Ohzaki K, Chaabouni H, Fryns J P, Desportes V, Beldjord C, Chelly J. 2002. ARX, a novel Prd-class-homeobox gene highly expressed in the telencephalon, is mutated in X-linked mental retardation. Hum Mol Genet 11:981-91.

Bolk, S, Angrist M, Schwartz S, Silvestri J M, Weese-Mayer D E, Chakravarti A. 1996. Congenital central hypoventilation syndrome: Mutation analysis of the receptor tyrosine kinase RET. Am J Med Gen 63:6035-609.

Bolk, S, Angrist M, Xie J, Yanagisawa M, Silvestri J M, Weese-Mayer D E, Chakravarti A. 1996. Endothelin-3 frameshift mutation in congenital central hypoventilation syndrome. Nature Genet 13:395-396.

Bower R J, Adkins J C. 1980. Ondine's curse and neurocristopathy. Clin Pediatr 19(10):665-668.

Cargill M. Altshuler D. Ireland J. Sklar P. Ardlie K. Patil N. Shaw N. Lane C R. Lim E P. Kalyanaraman N. Nemesh J. Ziaugra L. Friedland L. Rolfe A. Warrington J. Lipshutz R. Daley G Q. Lander E S. 1999. Characterization of single-nucleotide polymorphisms in coding regions of human genes. Nature Genetics 22:231-238.

Commare M. C., B. Francois, B. Estournet, and A. Barois. 1993. Ondine's curse: A discussion of five cases. Neuropediatrics. 24:313-318.

Dauger S, Renolleau S, Vardon G, Nepote V, Mas C, Simonneau M, Gaultier C, and Gallego J. 1999. Ventilatory responses to hypercapnia and hypoxia in Mash-I heterozygous newborn and adult mice. Pediatr Res 46:535-542.

Deonna T, Arczynska W, Torrado A. 1974. Congenital failure of automatic ventilation (Ondine's Curse). J Pediatr 84(5):710-714.

Devriendt K, Fryns J, Naulaers G, Devlieger H, Alliet P. 2000. Neuroblastoma in a mother and congenital central hypoventilation in her daughter: Variable expression of the same genetic disorder? Am J Med Genet 90:430-431.

Dubreuil V, Hirsch M, Jouve C, Brunet J, and Goridis C. 2002. The role of Phox2b in synchronizing pan-neuronal and type-specific aspects of neurogenesis. Development 129: 5241-5253.

Faure C, Viarme F, Cargill G, Navarro J, Gaultier C, and Trang H. 2002. Abnormal esophageal motility in children with congenital central hypoventilation syndrome. Gastroenterology 122:1258-1263.

Fitze G, Paditz E, Schlafke M, Kuhlisch E, Roesner D, Schackert H. 2003. Association of germline mutations and polymorphisms of the RET proto-oncogene with idiopathic congenital central hypoventilation syndrome in 33 patients. J Med Genet 40:E10.

Fleming P J, Cade D, Bryan M H, Bryan A C. 1980. Congenital central hypoventilation and sleep state. Pediatrics 66(3):425-428.

Gaultier C, Dauger S, Gallego J, Simonneau M, Trang-Pham H. 1999. Congenital central hypoventilation syndrome: A window on the genes involved in respiratory control. Medecine Sciences 15:851-856.

Gaultier C, Simonneau M, Dauger S, Gallego, J. 2003. Genetics and respiratory control: Studies in normal humans and genetically modified animals. Rev Mal Respir 20:77-94.

Glatt C E, DeYoung J A, Delgado S, Service S K, Giacomini K M, Edwards R H, Risch N, and N B Freimer. 2001. Screening a large reference sample to identify very low frequency sequence variants: comparisons between two genes. Nature Genet 27:435-438.

Goldberg D S, Ludwig I H. 1996. Congenital central hypoventilation syndrome: Ocular findings in 37 children. J Pediatr Ophthalmol Strabismus 33:175-180.

Goodman F R, Scambler P J. 2001. Human HOX gene mutations. Clinical Genetics 59:1-11.

Guilleminault C, McQuitty J, Ariagno R L, Challamel M J, Korobkin R, McClead, Jr. R E. 1982. Congenital central alveolar hypoventilation syndrome in six infants. Pediatrics 70(5):684-694.

Guillemot F and Joyner A. 1993. Dynamic expression of the murine Achaete-Scute homologue Mash-1 in the developing nervous system. Mechanisms of Development 42:171-185.

Guillemot F, Lo L, Johnson J E, Auerbach A, Anderson D J, and Joyner A L. 1993. Mammalian achaete-scute Homolog 1 is required for the early development of olfactory and autonomic neurons. Cell 75:463-478.

Haddad G G, Mazza N M, Defendini R, Blanc W A, Driscoll J M, Epstein MAF, Epstein R A, and Mellins R B. 1978. Congenital failure of automatic control of ventilation, gastrointestinal motility and heart rate. Medicine 57(6):517-526.

Hamill R W and LaGamma E F. 1999. Autonomic nervous system development in Autonomic Failure, 4th edition, editors Mathias and Bannister. Pp. 16-27.

Hamilton J, Bodurtha J N. 1989. Congenital central hypoventilation syndrome and Hirschsprung's disease in half sibs. J Med Genet 26:272-274.

Hirsch M, Tiveron M, Guillemot F, Brunet J, and Goridis C. 1998. Control of noradrenergic differentiation and Phox2a expression by MASH1 in the central and peripheral nervous system. Development 125:599-608.

Huber K, Combs S, Ernsberger U, Kalcheim C, and Unsicker K. 2002. Generation of neuroendocrine chromaffin cells from sympathoadrenal progenitors. Ann NY Acad Sci 971:554-559.

Johnson J E, Birren S J, and Anderson D J. 1990. Two rat homologues of *Drosophila* achaete-scute specifically expressed in neuronal precursors. Nature. 345:358-361.

Kanai M, Numakura C, Sasaki A, Shirahata E, Akaba K, Hashimoto M, Hasegawa H, Shiraswa S, Hayasaka K. Congenital central hypoventilation syndrome: a novel mutation of the RET gene in an isolated case. Tohoku J Exp Med 196: 241-246.

Khalifa M M, Flavin M A, Wherrett B A. 1988. Congenital central hypoventilation syndrome in monozygotic twins. J Pediatr 113:853-855.

Kitamura K, Yanazawa M, Sugiyama N, Miura H, Iizuka-Kogo A, Kusaka M, Omichi K, Suzuki R, Kato-Fukui Y, Kamiirisa K, Matsuo M, Kamijo S, Kasahara M, Yoshioka H, Ogata T, Fukuda T, Kondo I, Kato M, Dobyns W B, Yokoyama M, Morohashi K. 2002. Mutation of ARX causes abnormal development of forebrain and testes in mice and X-linked lissencephaly with abnormal genitalia in humans. Nat Genet 32:359-69.

Kuwaki T, Cao W, Kurihara Y, Kurihara H, Ling G, Onodera M, Ju K, Yazaki Y, and Kumada M. 1996. Impaired ventilatory responses to hypoxia and hypercapnia in mutant mice deficient in endothelin-1. Am J Physiol 270:R1279-R1286.

Lo L, Dormand E, Greenwood A, Anderson DJ. 2002. Comparison of the generic neuronal differentiation and neuron subtype specification functions of mammalian achaete-scute and atonal homologs in cultured neural progenitor cells. Development 129:1553-1567.

Lo L, Guillemot F, Joyner A, and Anderson DJ. 1994. MASH-1: A marker and a mutation for mammalian neural crest development. Perspectives on Develop Neurobiol 2:191-201.

Lo L, Johnson J E, Suenschell C W, Saito T, and Anderson D J. 1991. Mammalian achaete-scute homolog 1 is transiently expressed by spatially restricted subsets of early neuroepithelial and neural crest cells. Genes & Develop 5:1524-1537.

Lo L, Morin X, Brunet J, and Anderson DJ. 1999. Specification of neurotransmitter identity by Phox2 proteins in neural crest stem cells. Neuron 22:693-705.

Lo L, Sommer L, and Anderson DJ. 1997. MASH1 maintains competence for BPM2-induced neuronal differentiation in post-migratory neural crest cells. Current Biol 7:440-450.

Lo L, Tiveron M, and Anderson D J. 1998. MASH1 activates expression of the paired homeodomain transcription factor Phox2a, and couples pan-neuronal and subtype-specific components of autonomic neuronal identity. Development 125:609-620.

Marazita M L, Maher B S, Cooper M E, Silvestri J M, Huffman A D, Smok-Pearsall S M, Kowal M H, and Weese-Mayer D E. 2001. Genetic segregation analysis of autonomic nervous system dysfunction in families of probands with idiopathic congenital central hypoventilation syndrome. Am J Med Gen 100:229-236.

Matera I, Bachetti T, Cinti R, Lerone M, Gagliardi L, Morandi F, Motta M, Mosca F, Ottonello G, Piumelli R, Schober J G, Ravazzolo R, and Ceccherini I. 2002. Mutational analysis of the RNX gene in congenital central hypoventilation syndrome. Am J Med Gen 113:178-182.

Mellins R B, Balfour, Jr H H, Turino G M, Winters R W. 1970. Failure of automatic control of ventilation (Ondine's Curse). Medicine 49(6):487-504.

Minutillo C, Pemberton P J, Goldblatt J. 1989. Hirschsprung's disease and Ondine's curse: Further evidence for a distinct syndrome. Clin Genet 36:200-203.

Mukhopadhyay S. Wilkinson P W. 1990. Cerebral arterio-venous malformation, Ondine's curse and Hirschsprung's disease. Developmental Medicine & Child Neurology 32(12):1087-1089.

Nickerson D A, Tobe V O, Taylor S L. 1997. PolyPhred: automating the detection and genotyping of single nucleotide substitutions using fluorescence-based resequencing. Nucleic Acids Res 25:2745-2751.

O'Dell K, Staren S E, Bassuk A. 1987. Total colonic aganglionosis (Zuelzer-Wilson Syndrome) and congenital failure of automatic control of ventilation (Ondine's Curse). J Pediatr Surg 22:1019-1020.

Ogawa T, Kojo M, Fukushima N, Sonoda H, Goto K, Ishawa S, Ishiguro M. 1993. Cardio-respiratory control in an infant with Ondine's curse: a multivariate autoregressive modeling approach. J Autonomic Nerv Syst 42:41-52.

Paton J Y, Swaminathan S, Sargent C W, Keens T G. 1989. Hypoxic and hypercapnic ventilatory responses in awake children with congenital central hypoventilation syndrome. Am Rev Respir Dis 140:368-372.

Pattyn A, Morin X, Cremer H, Goridis C, and Brunet J. 1997. Expression and interactions of the closely related homeobox genes Phox2a and Phox2b during neurogenesis. Development 124:4065-4075.

Pattyn A, Morin X, Cremer H, Goridis C, and Brunet J. 1999. The homeobox gene Phox2b is essential for the development of autonomic neural crest derivatives. Nature 399: 366-370.

Pine D S, Weese-Mayer D E, Silvestri J M, Davies M, Whitaker A H, Klein D F. 1994. Anxiety and congenital central hypoventilation syndrome. Am J Psychiatry 151:864-870.

Renolleau S, Dauger S, Vardon G, Levacher B, Simonneau M, Yanagisawa M, Gaultier C, and Galleo J. 2001. Impaired ventilatory responses to hypoxia in mice deficient in endothelin-converting-enzyme-1. Pediatr Res 49:705-712.

Sakai T, Wakizaka A, Matsuda H, Nirasawa Y, Itoh Y. 1998. Point mutation in exon 12 of the receptor tyrosine kinase proto-oncogene RET in Ondine-Hirschsprung syndrome. Pediatrics. 101:924-926.

Sakai T, Wakizaka A, Nirasawa Y. 2001. Congenital central hypoventilation syndrome associated with Hirschsprung disease: Mutation analysis of the RET and endothelin-signaling pathways. Eur J Pediatr Surg 11:335-337.

Shannon D C, Marsland D W, Gould J B, Callahan B, Todres I D, Dennis J. 1976. Central hypoventilation during quiet sleep in two infants. Pediatrics 57 (3):342-346.

Shirasawa S, Arata A, Onimaru H, Roth K A, Brown G A, Horning S, Arata S, Okumura K, Sasazuki T, Korsmeyer S J. 2000. Rnx deficiency results in congenital central hypoventilation. Nature Genetics 24:287-290.

Silvestri J M, Chen M L, Weese-Mayer D E, McQuitty J M, Carveth H J, Nielson D W, Borowitz D, Cerny F. 2002. Idiopathic congenital central hypoventilation syndrome: The next generation. Am J Med Gen. 112:46-50.

Silvestri J M, Hanna B D, Volgman A S, Jones J P, Barnes S D, Weese-Mayer D E. 2000. Cardiac rhythm disturbances among children with idiopathic congenital central hypoventilation syndrome. Pediatr Pulmonol 29:351-358.

Silvestri J M, Weese-Mayer D E, Flanagan E A. 1995. Congenital central hypoventilation syndrome: Cardiorespiratory responses to moderate exercise, simulating daily activity. Pediatr Pulmonol 20(2):89-93.

Simon H H, Saueressig H, Wurst W, Goulding M D, O'Leary D D M. 2001. Fate of midbrain dopaminergic neurons controlled by the engrailed genes. J of Neurosci 21:3126-3134.

Sritippayawan S, Hamutcu R, Kun S S, Ner Z, Ponce M, Keens T G. 2002. Mother-daughter transmission of congenital central hypoventilation syndrome. Am J Respir Crit Care Med. 166: 367-369.

Staiano A, Santoro L, DeMarco R, Miele E, Fiorillo F, Auricchio A, Carpentieri M, Celli J, Auricchio S. 1999. Autonomic dysfunction in children with Hirschsprung's disease. Dig Dis Sci 44:960-965.

Stanke M, Junghans D, Geissen M, Goridis C, Ernsberger U and Rohrer H. 1999. The Phox2 homeodomain proteins are sufficient to promote the development of sympathetic neurons. Development 126:4087-4094.

Stromme P, Mangelsdorf M E, Shaw M A, Lower K M, Lewis S M, Bruyere H, Lutcherath V, Gedeon A K, Wallace R H, Scheffer I E, Turner G, Partington M, Frints S G, Fryns J P, Sutherland G R, Mulley J C, Gecz J. 2002. Mutations in the human ortholog of Aristaless cause X-linked mental retardation and epilepsy. Nat Genet 30:441-445.

Swaminathan S, Gilsanz V, Atkinson J, Keens T G. 1989. Congenital central hypoventilation syndrome associated with multiple ganglioneuromas. Chest 96:423-424.

Tam P, Chen B, Garcia-Barcelo M, Lui V, Ott J, Sham M. 2003. Association study of PHOX2b as a candidate gene for Hirschsprung's disease. Gut 52:563-567.

Verloes A, Elmer C, Lacombe D, Heinrichs C, Rebuffat E, Demarquez J L, Moncla A, Adam E. 1993. Ondine-Hirschsprung syndrome (Haddad syndrome): Further delineation in two cases and review of the literature. Eur J Pediatr 152:75-77.

Weese-Mayer D E, Bolk S, Silvestri J M, Chakravarti A. 2002. Idiopathic congenital central hypoventilation syndrome: Evaluation of brain-derived neurotrophic factor genomic DNA sequence variation. Am J Med Gen 107:306-310.

Weese-Mayer D E, Shannon D C, Keens T G, Silvestri J M. 1999. American Thoracic Society Statement on the diagnosis and management of idiopathic congenital central hypoventilation syndrome. Am J Respir Crit Care Med 160:368-373.

Weese-Mayer D E, Silvestri J M, Huffman A D, Smok-Pearsall S M, Kowal M H, Maher B S, Cooper M E, Marazita M L. 2001. Case/Control family study of ANS dysfunction in idiopathic congenital central hypoventilation syndrome. Am J Med Genet 100:237-245.

Weese-Mayer D E, Silvestri J M, Marazita M L, Hoo J J. 1993. Congenital central hypoventilation syndrome: Inheritance and relation to Sudden Infant Death Syndrome. Am J Med Genet 47:360-367.

Weese-Mayer D E, Silvestri J M, Menzies L J, Morrow-Kenny A S, Hunt C E, Hauptman S A. 1992. Congenital central hypoventilation syndrome: Diagnosis, management, and long-term outcome in thirty-two children. J Pediatr 120: 381-387.

Weese-Mayer D E, Berry-Kravis E M, Zhou L, Maher B S, Silvestri J M, Curran M E, Marazita M L. 2003. Idiopathic congenital central hypoventilation syndrome: Analysis of genes pertinent to early autonomic nervous system embryologic development and identification of mutations in PHOX2b. Am J Med Gen 123A:267-278.

Weese-Mayer D E, Berry-Kravis E M. 2004. Genetics of congenital central hypoventilation syndrome: Lessons from a seemingly orphan disease. Am J Respir Crit Care Med 170: 16-21, 2004.

Wells H H, Kattwinkel J, Morrow J D. 1980. Control of ventilation in Ondine's curse. J Pediatr 96(5):865-867.

Woo M S, Woo M A, Gozal D, Jansen M T, Keens T G, Harper R M. 1992. Heart rate variability in congenital central hypoventilation syndrome. Pediatr Res 31:291-296.

Young H M, Ciampoli D, Hsuan J, and Canty A J. 1999. Expression of Ret-p75NTR, Phox2a-, Phox2b-, and tyrosine hydroxylase-immunoreactivity by undifferentiated neural crest-derived cells and different classes of enteric neurons in the embryonic mouse gut. Developmental Dynamics 216: 137-152.

Zec N, Rowitch D H, Bitgood M J, and Kinney H C. 1997. Expression of the homeobox-containing genes EN 1 and EN2 in human fetal midgestational medulla and cerebellum. J Neuropathol and Exper Neurol 56:236-242.

While preferred embodiments have been illustrated and described, it should be understood that changes and modifications can be made therein in accordance with ordinary skill in the art without departing from the invention in its broader aspects as defined in the following claims.

---

What is claimed is:

1. A method of diagnosing or confirming idiopathic congenital central hypoventilation syndrome (CCHS) in a human subject, the method comprising
    (a) obtaining a nucleic acid sample from the subject;
    (b) amplifying the nucleic acid that includes the PHOX2b gene for the polyalanine repeat using a forward primer of SEQ ID NO: 4 and a reverse primer of SEQ ID NO: 5;
    (c) quantifying the length of the polyalanine repeat region of the PHOX2b gene; and
    (d) diagnosing or confirming CCHS based on the length of the polyalanine repeat region of PHOX2b.

2. The method of claim 1 wherein the sample comprises blood, white blood cells, epithelial cells, skin, hair, fibroblasts, a tissue from an organ, amniocytes, chorionic villi, embryonic cells, sperm and combinations thereof.

3. The method of claim 1 further comprising comparing the size of the PHOX2b gene against a known standard.

4. The method of claim 1 further comprising confirming whether the subject has the polyalanine mutation in the polyalanine repeat of the PHOX2b gene by sequencing the polyalanine repeat of the PHOX2b gene.

5. The method of claim 1 wherein the subject has a presumptive diagnosis of sudden infant death syndrome.

6. The method of claim 1 wherein the subject has Hirschprung's disease, alveolar hypoventilation, a tumor of neural crest origin and combinations thereof.

7. The method of claim 1 wherein the subject is an embryo or a fetus.

8. The method of claim 1 wherein the subject has late onset central hypoventilation syndrome.

9. The method of claim 1 further comprising determining whether a parent or a other relative of the subject has a polyalanine mutation in a polyalanine repeat of a PHOX2b gene or gene product.

10. The method of claim 1 further comprising determining whether the PHOX2b gene codes for a polyalanine mutation.

11. A method of determining whether an offspring of a human subject is at risk for idiopathic congenital central hypoventilation syndrome (CCHS) comprising:
(a) determining whether the subject has a polyalanine repeat expansion mutation in exon 3 of a human PHOX2b gene by a polymerase chain reaction (PCR) amplification using a forward primer of SEQ ID NO: 4 and a reverse primer of SEQ ID NO: 5, wherein the presence of the polyalanine repeat expansion mutation that encodes 25 to 33 alanine residues indicates that an offspring of the subject is at risk for CCHS.

\* \* \* \* \*

UNITED STATES PATENT AND TRADEMARK OFFICE
CERTIFICATE OF CORRECTION

PATENT NO. : 7,393,642 B2
APPLICATION NO. : 10/891585
DATED : July 1, 2008
INVENTOR(S) : Weese-Mayer et al.

Page 1 of 1

It is certified that error appears in the above-identified patent and that said Letters Patent is hereby corrected as shown below:

In Column 33, claim 1, line 63 should read as follows:

-- SEQ ID NO: 4 and a reverse primer of SEQ ID NO: 5; --

Signed and Sealed this

Thirtieth Day of June, 2009

JOHN DOLL
*Acting Director of the United States Patent and Trademark Office*

SEQUENCE LISTING

<160> NUMBER OF SEQ ID NOS: 11

<210> SEQ ID NO 1
<211> LENGTH: 4885
<212> TYPE: DNA
<213> ORGANISM: Homo sapiens
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t

<400> SEQUENCE: 1

```
ttaaatttta attagagatg caggatcaat gatagggagt tggacagttc agttccccag      60
tgccagccca atagacggat gagttatttt catgtaaaaa gcgccagcaa taagaccaac     120
cgtttgttat tgtcccaagt ggaaagagcc aagtttatta tgaggactat atggttttag     180
agacttcaga caaggcatnt cataggaggc tttttcataa aactaggntc tgctggtagt     240
aaggaggcca gtttggaggc aggcgttgag ctgtgcacat ctccccactc cagccacctt     300
ctccatatcc atcttttatt tcattttcc acttggctga gccatccaga accttttcaa      360
tgtataaaat ggaatattct tacctcaatt cctctgccta cgagtcctgt atggctggga     420
tggacacctc gagcctggct tcagcctatg ctgacttcag ttcctgcagc caggccagtg     480
gcttccagta taacccgata aggaccactt ttggggccac gtccggctgc ccttccctca     540
```

```
cgccgggatc ctgcagcctg gcaccctca gggaccacca gagcagtccg tacgccgcag    600
gtaaggacct tcagctttct cagcggagga agccgccttt ccgcccgtat ataggaagcc    660
ttgattgcat ttgaaaatgg aaatgtgttt agtatttacc aaacgaaatt tgcttacaca    720
aatgaaagaa tttatcacgt tagaagcgat tgcagggagg ggtaattcac ttacagggtt    780
acactatcct agtcacaccc gaaccgccaa caaaattatc ttaagctgcc aaaatgatag    840 gcataaattta tttactttgc gatgagacgt aaagcttaga aaataattaa ataacaaaga    900
gtaaagctca ttactggcag tgtctctttt tttaagaacc gacagcggct cacacctctt    960
tggctggtca tttttatgat tatttcttta atttattatt attttttttgc agctctttcc   1020 cccaactttt gagccgggtc aactttctga gaattgaaaa gttcccaaag tgggactgtt   1080
tggtaacttc tttcctggct ccctgatatt ccgactgatg ttttttggatt tttttcctct   1140 ctggtttttt cctgctgaaa gcactatctc aagtccgtca catcgcgctg tttcaatcca   1200
cccaaaggcg cttgtgccag aaaggactcc gccaagcccg aagtttgagc ccaggtttcc   1260
gcagataaca aatttcctcg gtttcttccc gcagcttctc tcggcaactc tctcgcgcgg   1320
gtgtaggtag cggctgccgt atgacctgac cttggagtcc tcacattcta gctccacggc   1380
cggcgagctg ccggctgatt tgctcacttt ctgtctcctc tgtcatactc tagttcctta   1440
caaactcttc acggaccacg gcggcctcaa cgagaagcgc aagcagcggc gcatccgcac   1500
cactttcacc agtgcccagc tcaaagagct ggaaagggtc ttcgcggaga ctcactaccc   1560
cgacatctac actcggagg agctggccct gaagatcgac ctcacagagg cgcgagtcca   1620
ggtacgcgcg cctggaaacc gaccccgctc cgccgcactg gtccggggag gtgtgggggtg   1680 aggggcggct ggtaaattcg aagtcctgga gcctcgagtg agaaggacct agggcccat   1740 ggccgatcag aaatactgga tttggtgtgg ctgtgcgttc gagagaggct tagagcgcac   1800
gctcttggca ttttatttac agttgcgaag tgtttcccac ccgagcagag acatgggggg   1860
ccttgggacg tggatgagcg atgcaatttc ggggacagga agtgcctgtg gtggaaggtg   1920
tgcagacttt gctcccgtat tataagtttt tccttctccc ctcccgcccc ccaaaaaaat   1980
gcctcctaac tcaagtgctt ttaacctggc cccatggcat ataggttcat tttcccggaa   2040
actgtgactt gcatcagatt tgcaaagggt ctgtgacttc atgaaggtca agaaccatga   2100
cttactccaa cctgttaaac acaggtgcgc tcacgagttg gccacagcgc ctctctgggt   2160
gagcccccga ccgagaagcg gtgcgcacca tcgcacgctc ttccaggctc aaaggccggg   2220
gatgggcagc ggagcaaacc cagaggatcc cttttccttc taccaattag agtttaactt   2280
tagaacttag gcttaggggt gaatggcgag ctcggggctt gctcaagaag ccgacttgaa   2340
cagaggccca ccaaaataag gccttccctt ttcgggtctt tctgggacct gcggcttttt   2400
aaactctgcc gcaagccttc atgtccctgg cgtgctcact cccctaaga agtttctcc   2460 gaaaatgcac agcaataaga agcggtagac ttggtggatg tgcgcgcggg ggtgatcaca   2520
gcgcatgggg aggagggtgt taaaacaagc cgaagtagaa cttgggccac cctaaccggt   2580
gcttttcttt cccatttctct tctttctccc cctgcttcac cgtctctcct tccgtcttgg   2640
gccaggtgtg gttccagaac cgccgcgcca agtttcgcaa gcaggagcgc gcagcggcag   2700
ccgcagcggc cgcggccaag aacggctcct cgggcaaaaa gtctgactct tccagggacg   2760
acgagagcaa agaggccaag agcactgacc cggacagcac tgggggccca ggtcccaatc   2820
ccaaccccac ccccagctgc ggggcgaatg gaggcggcgg cggcggggccc agcccggctg   2880
```

-continued

```
gagctccggg ggcggcgggg cccgggggcc cgggaggcga acccggcaag ggcggcgcag    2940
cagcagcggc ggcggccgcg gcagcggcgg cggcggcagc ggcagcggcg gcagctggag    3000
gcctggctgc ggctggggc cctggacaag gctgggctcc cggccccggc cccatcacct    3060
ccatcccgga ttcgcttggg ggtcccttcg gcagcgtcct atcttcgctc caaagaccca    3120
acggtgccaa agccgcctta gtgaagagca gtatgttctg atctggaatc ctgcggcggc    3180
ggcggcggcg gcgacagcgg gcgagccagg gcccgggcgg gcgagtgggc gagcgggtag    3240
gcccaaggct attgtcgtcg ctgctgccat ggcttttca ttgagggcct aaagtaatcg    3300
cgctaagaat aaagggaaaa cggcgtcgcc ctcatttcaa ccccactcct acccccttcc    3360
tcaacccca acaaaacaa acaaacttcc ctggcttcgc acctgcctgg ggcctcgcag    3420
cggggccagg gctccgcctg ctgatcgggg gttgtgagca gcgcggcctg gacgcggggc    3480
actctcaggg ggctgtgtct gcgtgtcagt ttgtgtctgt ctcggggaat gtgtgtctgt    3540
ggcccaagca ggtgacagga agagatgggg ggcctcaacc aacttagtga cttgtttaga    3600
aaaaaaagac aaaaaagtaa aaataaaaac aaaaaagttg gaaggcagaa accattaaaa    3660
aacaaaaagc caacaaccca gaaaggttta aaaaacataa ggaaaaaaaa gacaaattaa    3720
aggagggggct aggggagaag ctgcagctgg agctgaaggc tcgatcttgt gaaccctaa    3780
atccgctccc tcctaacagc acggattctc ttggggctct tcttcaggga agagtaggga    3840
cgccgttcca gccccccttc ctatcgtgtc cttgggttcg ggtcactgcg gcgacgactt    3900
gctcagactg tccggcggc cggagtgact ttctcgcacc cccttgcctg tcccacctcg    3960
ctgaacacca tcccgccatt agcgcatcgg aaccccacac agttgcaact cccaaccccg    4020
aatctttgca gccgttcggc cctgaaagat gccctatcca tgagatgcct tttcatctgc    4080
aaactctgca aaatgtgtct catgtttcgc aactcttttt ttcccctcg ctcccgccta    4140
ccccgtcggc attttcttct tccaccagct tttactgaac ttttttggcac tgctttggat    4200
tggggtcaat tgcagtccac gtaactggct gcagagaaat ctaccgagca aggaaaaggc    4260
acacacacac gttgcaggg gtgtctcggt ttgcatttct gttggaatga tccgaactgg    4320
actcacatcc tgtatggtgg atggactgta tattgagggt tccattcttc gcgcagttta    4380
gacatctctg ttttgattct ttgttgttgt ttttatttta aaaggcacaa actctagata    4440
ttagttgaat gttgaggctt taactttttc ggtgtctttc tacaactgtg ttctgtgact    4500
caattgtatc gtgttaatat cagtgcagac tgtctcctct acgtgaccgt ataatgtttt    4560
tctcgtcttg tagtctctat ggcgtgtctt tatggtgtaa taaggttctc acgggtcaa    4620
tcttttgtgt ttagagaggc cacggttcag acaatggtat atatttttgt tatcaggtgc    4680
atgtctgtct gatttctttt tttttcctgt tggactatgt ttgtgaacat aattgtcata    4740
agttatgttt cagattttg aatttattta tatgtgttat aatgaatgct tctatttaaa    4800
agggaaatat ttctacatgt gcttatagtt ttccaagagt gtaccattaa cttgattgtt    4860
gataataaaa accaaaagca agtct                                          4885
```

<210> SEQ ID NO 2
<211> LENGTH: 314
<212> TYPE: PRT
<213> ORGANISM: Homo sapiens

<400> SEQUENCE: 2

Met Tyr Lys Met Glu Tyr Ser Tyr Leu Asn Ser Ser Ala Tyr Glu Ser
1               5                   10                  15

```
Cys Met Ala Gly Met Asp Thr Ser Ser Leu Ala Ser Ala Tyr Ala Asp
                20                  25                  30

Phe Ser Ser Cys Ser Gln Ala Ser Gly Phe Gln Tyr Asn Pro Ile Arg
            35                  40                  45

Thr Thr Phe Gly Ala Thr Ser Gly Cys Pro Ser Leu Thr Pro Gly Ser
        50                  55                  60

Cys Ser Leu Gly Thr Leu Arg Asp His Gln Ser Ser Pro Tyr Ala Ala
 65                  70                  75                  80

Val Pro Tyr Lys Leu Phe Thr Asp His Gly Leu Asn Glu Lys Arg
                85                  90                  95

Lys Gln Arg Arg Ile Arg Thr Thr Phe Thr Ser Ala Gln Leu Lys Glu
                100                 105                 110

Leu Glu Arg Val Phe Ala Glu Thr His Tyr Pro Asp Ile Tyr Thr Arg
            115                 120                 125

Glu Glu Leu Ala Leu Lys Ile Asp Leu Thr Glu Ala Arg Val Gln Val
        130                 135                 140

Trp Phe Gln Asn Arg Arg Ala Lys Phe Arg Lys Gln Glu Arg Ala Ala
145                 150                 155                 160

Ala Ala Ala Ala Ala Ala Lys Asn Gly Ser Ser Gly Lys Lys Ser
                165                 170                 175

Asp Ser Ser Arg Asp Asp Glu Ser Lys Glu Ala Lys Ser Thr Asp Pro
                180                 185                 190

Asp Ser Thr Gly Gly Pro Gly Pro Asn Pro Asn Pro Thr Pro Ser Cys
            195                 200                 205

Gly Ala Asn Gly Gly Gly Gly Gly Pro Ser Pro Ala Gly Ala Pro
        210                 215                 220

Gly Ala Ala Gly Pro Gly Pro Gly Gly Glu Pro Gly Lys Gly Gly
225                 230                 235                 240

Ala Ala Ala Ala Ala Ala Ala Ala Ala Ala Ala Ala Ala Ala
                245                 250                 255

Ala Ala Ala Ala Gly Gly Leu Ala Ala Ala Gly Gly Pro Gly Gln Gly
            260                 265                 270

Trp Ala Pro Gly Pro Gly Pro Ile Thr Ser Ile Pro Asp Ser Leu Gly
            275                 280                 285

Gly Pro Phe Gly Ser Val Leu Ser Ser Leu Gln Arg Pro Asn Gly Ala
        290                 295                 300

Lys Ala Ala Leu Val Lys Ser Ser Met Phe
305                 310

<210> SEQ ID NO 3
<211> LENGTH: 314
<212> TYPE: PRT
<213> ORGANISM: Mus musculus

<400> SEQUENCE: 3

Met Tyr Lys Met Glu Tyr Ser Tyr Leu Asn Ser Ser Ala Tyr Glu Ser
  1               5                  10                  15

Cys Met Ala Gly Met Asp Thr Ser Ser Leu Ala Ser Ala Tyr Ala Asp
                20                  25                  30

Phe Ser Ser Cys Ser Gln Ala Ser Gly Phe Gln Tyr Asn Pro Ile Arg
            35                  40                  45

Thr Thr Phe Gly Ala Thr Ser Gly Cys Pro Ser Leu Thr Pro Gly Ser
        50                  55                  60

Cys Ser Leu Gly Thr Leu Arg Asp His Gln Ser Ser Pro Tyr Ala Ala
 65                  70                  75                  80
```

Val Pro Tyr Lys Leu Phe Thr Asp His Gly Gly Leu Asn Glu Lys Arg
                85                  90                  95

Lys Gln Arg Arg Ile Arg Thr Phe Thr Ser Ala Gln Leu Lys Glu
            100                 105                 110

Leu Glu Arg Val Phe Ala Glu Thr His Tyr Pro Asp Ile Tyr Thr Arg
            115                 120                 125

Glu Glu Leu Ala Leu Lys Ile Asp Leu Thr Glu Ala Arg Val Gln Val
            130                 135                 140

Trp Phe Gln Asn Arg Arg Ala Lys Phe Arg Lys Gln Glu Arg Ala Ala
145                 150                 155                 160

Ala Ala Ala Ala Ala Ala Lys Asn Gly Ser Ser Gly Lys Lys Ser
            165                 170                 175

Asp Ser Ser Arg Asp Asp Glu Ser Glu Ala Lys Ser Thr Asp Pro
            180                 185                 190

Asp Ser Thr Gly Gly Pro Gly Pro Asn Pro Asn Pro Thr Pro Ser Cys
            195                 200                 205

Gly Ala Asn Gly Gly Gly Gly Gly Pro Ser Pro Ala Gly Ala Pro
210                 215                 220

Gly Ala Ala Gly Pro Gly Gly Pro Gly Gly Glu Pro Gly Lys Gly Gly
225                 230                 235                 240

Ala Ala Ala Ala Ala Ala Ala Ala Ala Ala Ala Ala Ala Ala Ala
            245                 250                 255

Ala Ala Ala Ala Gly Gly Leu Ala Ala Gly Gly Pro Gly Gln Gly
            260                 265                 270

Trp Ala Pro Gly Pro Gly Pro Ile Thr Ser Ile Pro Asp Ser Leu Gly
            275                 280                 285

Gly Pro Phe Ala Ser Val Leu Ser Ser Leu Gln Arg Pro Asn Gly Ala
            290                 295                 300

Lys Ala Ala Leu Val Lys Ser Ser Met Phe
305                 310

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
ccaggtccca atcccaac                                                 18

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
gagcccagcc ttgtccag                                                 18

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6

```
gacctcagac aaggcatctc a                                            21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aattacccct ccctgcaatc                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ctgccgtatg acctgacctt                                              20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
acagccacac caaatccagt                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
accctaaccg gtgcttttct                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
acaatagcct tgggcctacc                                              20
```